(12) United States Patent
Gorin et al.

(10) Patent No.: US 11,713,298 B2
(45) Date of Patent: Aug. 1, 2023

(54) PROCESS FOR PREPARING 2-[[5-(3-CHLOROPHENYL)-3-HYDROXYPYRIDINE-2-CARBONYL]AMINO]ACETIC ACID

(71) Applicant: Akebia Therapeutics, Inc., Cambridge, MA (US)

(72) Inventors: Boris I. Gorin, Cambridge, MA (US); Christopher M. Lanthier, Cambridge, MA (US); Anne Buu Chau Luong, Cambridge, MA (US); James Densmore Copp, Cambridge, MA (US); Javier Gonzalez, Cambridge, MA (US)

(73) Assignee: Akebia Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/053,614

(22) PCT Filed: May 8, 2019

(86) PCT No.: PCT/US2019/031310
§ 371 (c)(1),
(2) Date: Nov. 6, 2020

(87) PCT Pub. No.: WO2019/217550
PCT Pub. Date: Nov. 14, 2019

(65) Prior Publication Data
US 2021/0070709 A1    Mar. 11, 2021

Related U.S. Application Data

(60) Provisional application No. 62/669,135, filed on May 9, 2018.

(51) Int. Cl.
*C07D 213/81* (2006.01)

(52) U.S. Cl.
CPC .................................. *C07D 213/81* (2013.01)

(58) Field of Classification Search
CPC .................................................. C07D 213/81
USPC ......................................................... 546/298
See application file for complete search history.

(56) References Cited

U.S. PATENT DOCUMENTS

| | | |
|---|---|---|
| 3,655,679 A | 4/1972 | Tsung-ying et al. |
| 3,703,582 A | 11/1972 | Shen et al. |
| 3,894,920 A | 7/1975 | Kondo et al. |
| 4,016,287 A | 4/1977 | Ebhardt et al. |
| 5,397,799 A | 3/1995 | Kress et al. |
| 5,405,613 A | 4/1995 | Rowland et al. |
| 5,607,954 A | 3/1997 | Weidmann et al. |
| 5,610,172 A | 3/1997 | Weidmann et al. |
| 5,620,995 A | 4/1997 | Weidmann et al. |
| 5,620,996 A | 4/1997 | Weidmann et al. |
| 5,658,933 A | 8/1997 | Weidemann et al. |
| 5,719,164 A | 2/1998 | Weidmann et al. |
| 5,726,305 A | 3/1998 | Weidmann et al. |
| 6,020,350 A | 2/2000 | Wiedmann et al. |
| 6,093,730 A | 7/2000 | Weidmann et al. |
| 6,159,379 A | 12/2000 | Means et al. |
| 6,420,427 B1 | 7/2002 | Takahashi et al. |
| 6,566,088 B1 | 5/2003 | McKnight et al. |
| 6,589,758 B1 | 7/2003 | Zhu |
| 7,183,287 B2 | 2/2007 | Durley |
| 7,323,475 B2 | 1/2008 | Arend et al. |
| 7,588,924 B2 | 9/2009 | Evdokimov et al. |
| 7,811,595 B2 | 10/2010 | Kawamoto et al. |
| 8,050,873 B2 | 11/2011 | Evdokimov et al. |
| 8,124,582 B2 | 2/2012 | Guenzler-Pukall et al. |
| 8,129,376 B2 | 3/2012 | Sundaresan et al. |
| 8,273,773 B2 | 9/2012 | Brameld et al. |
| 8,323,671 B2 | 12/2012 | Wu et al. |
| 8,343,952 B2 | 1/2013 | Kawamoto et al. |
| 8,512,972 B2 | 8/2013 | Evdokimov et al. |
| 8,530,404 B2 | 9/2013 | Seeley et al. |
| 8,598,210 B2 | 12/2013 | Kawamoto et al. |

(Continued)

FOREIGN PATENT DOCUMENTS

| | | |
|---|---|---|
| CA | 2098158 | 6/1993 |
| CA | 2253282 | 11/1997 |

(Continued)

OTHER PUBLICATIONS

U.S. Appl. No. 16/921,273, filed Jul. 6, 2020, Lanthier et al.

(Continued)

*Primary Examiner* — Niloofar Rahmani
(74) *Attorney, Agent, or Firm* — Proskauer Rose LLP; Fangli Chen

(57) ABSTRACT

Disclosed herein are methods and processes of preparing vadadustat and pharmaceutically acceptable salts thereof, and intermediates of formula (I) and their salts useful for the synthesis of vadadustat.

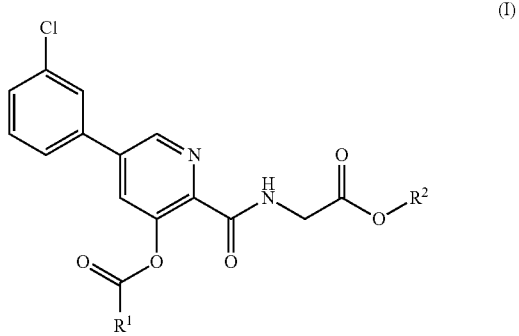

(I)

17 Claims, No Drawings

(56) References Cited

U.S. PATENT DOCUMENTS

| | | |
|---|---|---|
| 8,722,895 B2 | 5/2014 | Kawamoto et al. |
| 8,865,748 B2 | 10/2014 | Shalwitz et al. |
| 8,940,773 B2 | 1/2015 | Kawamoto et al. |
| 9,145,366 B2 | 9/2015 | Lanthier et al. |
| 9,598,370 B2 | 3/2017 | Kawamoto et al. |
| 9,701,636 B2 | 7/2017 | Copp et al. |
| 9,776,969 B2 | 10/2017 | Lanthier et al. |
| 9,987,262 B2 | 6/2018 | Copp et al. |
| 10,149,842 B2 | 12/2018 | Copp et al. |
| 10,246,416 B2 | 4/2019 | Lanthier et al. |
| RE47,437 E | 6/2019 | Kawamoto et al. |
| 10,596,158 B2 | 3/2020 | Copp et al. |
| 10,729,681 B2 | 8/2020 | Kawamoto et al. |
| 10,738,010 B2 | 8/2020 | Lanthier et al. |
| 2002/0192737 A1 | 12/2002 | Kaelin, Jr. et al. |
| 2003/0153503 A1 | 8/2003 | Klaus et al. |
| 2003/0176317 A1 | 9/2003 | Guenzler-Pukall et al. |
| 2004/0235082 A1 | 11/2004 | Foumey et al. |
| 2004/0254215 A1 | 12/2004 | Arend et al. |
| 2006/0142389 A1 | 6/2006 | Aurell et al. |
| 2006/0276477 A1 | 12/2006 | Klaus et al. |
| 2007/0105899 A1 | 5/2007 | Suzuki et al. |
| 2007/0154482 A1 | 7/2007 | Sukhatme et al. |
| 2007/0203174 A1 | 8/2007 | Klimko et al. |
| 2007/0213335 A1 | 9/2007 | Fitch et al. |
| 2007/0299086 A1 | 12/2007 | Kawamoto et al. |
| 2008/0124740 A1 | 5/2008 | Evkokimov et al. |
| 2008/0213404 A1 | 9/2008 | Johnson et al. |
| 2009/0023666 A1 | 1/2009 | Gardiner et al. |
| 2009/0082357 A1 | 3/2009 | Fitch et al. |
| 2009/0240475 A1 | 9/2009 | Evdokimov et al. |
| 2010/0021423 A1 | 1/2010 | Brameld et al. |
| 2010/0331303 A1 | 12/2010 | Kawamoto et al. |
| 2010/0331374 A1 | 12/2010 | Wu et al. |
| 2011/0077400 A1 | 3/2011 | Lobben et al. |
| 2011/0305776 A1 | 12/2011 | Ho et al. |
| 2012/0282627 A1 | 11/2012 | Evdokimov et al. |
| 2012/0309977 A1 | 12/2012 | Lanthier et al. |
| 2012/0316204 A1 | 12/2012 | Shalwitz et al. |
| 2012/0329836 A1 | 12/2012 | Marsh et al. |
| 2013/0022974 A1 | 1/2013 | Chinnaiyan et al. |
| 2013/0203816 A1 | 8/2013 | Kawamoto et al. |
| 2013/0245076 A1 | 9/2013 | Kawamoto et al. |
| 2014/0045899 A1 | 2/2014 | Kawamoto et al. |
| 2014/0057892 A1 | 2/2014 | Kawamoto et al. |
| 2015/0119425 A1 | 4/2015 | Kawamoto et al. |
| 2015/0141467 A1 | 5/2015 | Copp |
| 2015/0361043 A1 | 12/2015 | Lanthier et al. |
| 2016/0009648 A1 | 1/2016 | Kawamoto et al. |
| 2016/0143891 A1 | 5/2016 | Shalwitz et al. |
| 2016/0199434 A1 | 7/2016 | Eubank et al. |
| 2016/0214939 A1 | 7/2016 | Hanselmann et al. |
| 2016/0339005 A1 | 11/2016 | Shalwitz et al. |
| 2017/0189387 A1 | 7/2017 | Kawamoto et al. |
| 2017/0258773 A1 | 9/2017 | Copp et al. |
| 2017/0362178 A1 | 12/2017 | Lanthier et al. |
| 2018/0065933 A1 | 3/2018 | Hanselmann et al. |
| 2018/0092892 A1 | 4/2018 | Smith et al. |
| 2018/0280365 A1 | 10/2018 | Copp et al. |
| 2019/0192494 A1 | 6/2019 | Kawamoto et al. |
| 2020/0345711 A1 | 11/2020 | Copp et al. |
| 2021/0122715 A1 | 4/2021 | Lanthier et al. |
| 2021/0137901 A1 | 5/2021 | Kawamoto et al. |
| 2021/0206721 A1 | 7/2021 | Ranjan et al. |

FOREIGN PATENT DOCUMENTS

| | | |
|---|---|---|
| CN | 105837502 A | 8/2016 |
| CN | 111320577 A | 6/2020 |
| EP | 0650960 | 5/1995 |
| EP | 0650961 | 5/1995 |
| EP | 2044005 | 10/2010 |
| EP | 3290404 | 7/2018 |
| JP | H09221476 | 8/1997 |
| JP | 2001-48786 | 2/2001 |
| JP | 2007-194072 | 11/2006 |
| JP | 2010-527378 | 11/2009 |
| WO | WO 1996/022021 | 7/1996 |
| WO | WO 1997/041103 | 11/1997 |
| WO | WO 1997/044333 | 11/1997 |
| WO | WO 1999/048870 | 11/1999 |
| WO | WO 2002/074980 | 9/2002 |
| WO | WO 2002/074981 | 9/2002 |
| WO | WO 2002/083688 | 10/2002 |
| WO | WO 2003/028663 | 4/2003 |
| WO | WO 2003/032972 | 4/2003 |
| WO | WO 2003/049686 | 6/2003 |
| WO | WO 2003/053997 | 7/2003 |
| WO | WO 2003/097040 | 11/2003 |
| WO | WO 2004/019868 | 3/2004 |
| WO | WO 2004/035812 | 4/2004 |
| WO | WO 2004/048383 | 6/2004 |
| WO | WO 2004/108121 | 12/2004 |
| WO | WO 2005/007192 | 1/2005 |
| WO | WO 2005/115984 | 12/2005 |
| WO | WO 2005/118836 | 12/2005 |
| WO | WO 2006/019831 | 2/2006 |
| WO | WO 2006/030977 | 3/2006 |
| WO | WO 2006/114213 | 11/2006 |
| WO | WO 2007/047194 | 4/2007 |
| WO | WO 2007/070359 | 6/2007 |
| WO | WO 2007/082899 | 7/2007 |
| WO | WO 2007/084667 | 7/2007 |
| WO | WO 2007/088571 | 8/2007 |
| WO | WO 2007/103905 | 9/2007 |
| WO | WO 2007/136990 | 11/2007 |
| WO | WO 2007/150011 | 12/2007 |
| WO | WO 2008/002576 | 1/2008 |
| WO | WO 2008/089051 | 7/2008 |
| WO | WO 2008/089052 | 7/2008 |
| WO | WO 2009/020119 | 8/2008 |
| WO | WO 2008/130508 | 10/2008 |
| WO | WO 2008/130527 | 10/2008 |
| WO | WO 2008/137060 | 11/2008 |
| WO | WO 2008/141731 | 11/2008 |
| WO | WO 2008/144266 | 11/2008 |
| WO | WO 2009/019656 | 2/2009 |
| WO | WO 2009/035534 | 3/2009 |
| WO | WO 2009/037570 | 3/2009 |
| WO | WO 2009/039321 | 3/2009 |
| WO | WO 2009/039323 | 3/2009 |
| WO | WO 2007/038571 | 4/2009 |
| WO | WO 2009/043093 | 4/2009 |
| WO | WO 2009/049112 | 4/2009 |
| WO | WO 2009/067790 | 4/2009 |
| WO | WO 2009/070644 | 6/2009 |
| WO | WO 2009/073497 | 6/2009 |
| WO | WO 2009/073669 | 6/2009 |
| WO | WO 2009/086044 | 7/2009 |
| WO | WO 2009/086592 | 7/2009 |
| WO | WO 2009/089547 | 7/2009 |
| WO | WO 2009/111337 | 9/2009 |
| WO | WO 2010/029577 | 3/2010 |
| WO | WO 2010/113942 | 10/2010 |
| WO | WO 2011/057112 | 11/2010 |
| WO | WO 2012/170377 | 12/2012 |
| WO | WO 2012/170439 | 12/2012 |
| WO | WO 2012/170442 | 12/2012 |
| WO | WO 2013/013609 | 1/2013 |
| WO | WO 2014/168986 | 10/2014 |
| WO | WO 2014/200773 | 12/2014 |
| WO | WO 2015/023967 | 2/2015 |
| WO | WO 2015/073779 | 5/2015 |
| WO | WO 2015/112831 | 7/2015 |
| WO | WO 2016/118858 | 7/2016 |
| WO | WO 2016/153996 | 9/2016 |
| WO | WO 2016/161094 | 10/2016 |
| WO | WO 2006/138511 | 12/2016 |
| WO | WO 2019/217550 | 11/2019 |
| WO | WO 2021/087144 | 5/2021 |
| WO | WO 2021/188936 | 9/2021 |

(56) References Cited

FOREIGN PATENT DOCUMENTS

WO  WO 2021/188938  9/2021
WO  WO 2021/188944  9/2021

OTHER PUBLICATIONS

"Akebia closes $41 million series C—Proceeds to support phase 2b trial and phase 3 preparations for promising anemia candidate", 2013; retrieved from the internet on Jan. 22, 2018.
Acker et al., "Genetic evidence for a tumor suppressor role of HIF-2α", Cancer Cell, 8:131-141 (2005).
Alesso et al., "Improving resins for solid phase synthesis: incorporation of I-[2-(2-methoxvethoxv) ethoxv]4-vinvl-benzene" Tetrahedron: 59: 7163-7169 (2003).
Altschul et al., "Gapped BLAST and PSI-BLAST: A New Generation of Protein Database Search Programs," Nucleic Acids Res., 25(27): 3389-3402 (1997).
Anderson et al., "Antileukemic Activity of Derivatives of I,2-Dimethyl-3,4-bis(hydroxvmethyl)-5-phenylpyrrole Bis(N-methylcarbamate)", J. Med. Chem., 22(8): 977-980 (1979).
Anderson et al., "Practical process research and development: a guide for organic chemists", p. 331. (2012).
Annex et al., "Growth Factor-Induced Therapeutic Angiogenesis in the Heart: Protein Therapy," Cardiovascular Research, 65(3): 649-655 (2005).
Ardelt et al., "Estradiol Regulates Angiopoietin-1 mRNA Expression Through Estrogen Receptor-a in a Rodent Experimental Stroke Model," Stroke, 36: 337-341 (2005).
Auerbach et al., "Angiogenesis Assays: A Critical Overview," Clinical Chemistry, 49: 32-40 (2003).
Barany et al., "Solid-phase Peptide Synthesis: A Silver Anniversary Report," Int. J. Peptide Protein Res., 30(6): 705-739 (1987).
Bartlett et al., "Caveat: A Program to Facilitate the Structure-derived Design of Biologically Active Molecules", Molecular Recognition in Chemical and Biological Problems, Special Pub., Royal Chem. Soc., 78: 182-196 (Apr. 1989).
Bohm, "The Computer Program LUDI: A New Method for the Novo Design of Enzyme Inhibitors," J. Computer-Aided Molecular Design, 6: 61-78 (1992).
Branden et al., "Introduction to Protein Structure Second Edition," Garland Publishing, Inc., New York: 374-375 (1999).
Brittain et al., "Polymorphism in Pharmaceutical Solids." Drugs and the Pharmaceutical Sciences, 2nd Edition, Edited by Brittain H.G., 192: 333-335 (2009).
Burger, "Isosterism and biososterism in drug design", Progress in Drug Research, Birkhauser Verlag (1991).
Bussolino, "Molecular Mechanisms of Blood Vessel Formation," Trends Biochem. Sci., 22(7): 251-256 (1997).
Byrn et al., "Pharmaceutical Solids: A Strategic Approach to Regularity Considerations", Pharmaceutical Research, 12(7): 945-954 (1995).
Carey, FA., Organic Chemistry 6th Ed. McGraw Hill, chapter 1, p. 9, chapter 19, pp. 839-840 and chapter 27, pp. 1182-1183 (2006).
CAS Registry Nos. 1261773-17-4, 1261723-73-2. Chemcats, 2 pages (2011).
CAS Registry Nos. 1261813-98-2, 1261613-86-8, and 1261518-21-1. Chemcats, (2011).
CAS Registry Nos. 1361609-40-6, 1361556-21-9, 1361555-42-1, 1361544-77-5, 1361480-63-8, 1361477-92-0. Chemcats, 6 pages (2012).
CAS Registry Nos. 1361809-77-9, 1361737-20-3, 1361721-11-0, 1361693-45-9, 1361676-79-0. Chemcats, 5 pages (2012).
Catrina et al., "Hyperglycemia Regulates Hypoxia-Inducible Factor-Ia Protein Stability and Function," Diabetes 53: 3226-3232 (2004).
Cheeseright, "The Identification of Bioisosteres as Drug Development Candidates", Innovations in Pharmaceutical Technology, issue 28 (2009).

Cherng, "Synthesis of substituted pryidines by the reactions of halopyridines with sulfur, oxygen and carbon nucleophiles under focused microwave irradition", Tetrahedron, Jun. 10, 2002, 58(24): 4931-4935 (2002).
Clinicaltrials.gov: archive: NCT01235936 Nn 2012_09_30[online]. U.S. National Institute of Health, Aug. 30, 2012; retrieved from the internet at <http:clinicaltrials.gov/archive/NCT01235936/2012_09_30> (Aug. 30, 2012).
Costello et al., "Evidence for changes in RREB-1, ZIP3, and zinc in the early development of pancreatic adenocarcinoma", J Gastrointest Canc, 43: 570-578 (2012).
Cousins, "Retina Today", 2 pages; retrieved from the internet at http://retinatoday.com/2009/10/1009_12.php (Oct. 2009).
Cunliffe et al., "Novel Inhibitors of Prolyl4-Hydroxylase. 3. Inhibition by the Substrate Analoe:ue N-Oxaloglycine and Its Derivatives," J. Med. Chem. 35: 2652-2658 (1992).
"Standards of Medical Care in Diabetes—2006", Diabetes Care, 29: s4-s42 (2006).
Demetriades et al., "Dynamic combinatorial chemistry employing embryonic boronic acids/boronate esters leads to potent oxygenase inhibitors", Angewandte Chemie, International Edition, May 25, 2012, 51(27): 6672-6675 (2012).
Dranoff, "GM-CSP-secreting melanoma vaccines", Oncogene, 22: 3188-3192 (2003).
Elson et al., "Induction of hypervascularity without leakage or inflammation in transgenic mice overexpressing hypoxia-inducible factor-1α," Genes & Dev., 15: 2520-2532 (2001).
Elvidge et al., "Concordant Regulation of Gene Expression by Hypoxia and 2-Oxoglutarate-dependent Dioxygenase Inhibition", J. Biol. Chem., 281(22): 15215-15226 (2006).
Enoch et al., "ABC of wound healing. Non-surgical and drug treatments", BMJ, 332(7546):332:900-3 (2006).
Favier et ai., "HIF2αreduces growth rate but promotes angiogenesis in a mouse model of neuroblastoma", BMC Cancer, 7:139: 1-10 (2007).
Flower, "Modelling G-protein-coupled receptors fordrug design," Biochimica et Biophysics Acta, 1422: 207-234 (1999).
Folkman et al., "Tumor Angiogenesis," The Molecular Basis of Cancer, Mendelsohn et al., eds., W. B. Saunders, Chapter 10: 206-232 (1995).
Franklin et al., "Approaches to the Design of Anti-Fibrotic Drugs," Biochem. Soc. Trans., 19(4): 812-5 (Nov. 1991).
Gaunt, "Rational Design of Benzyl-Type Protecting Groups Allows Sequential Deprotection of Hvdroxyl Groups by Catalytic Hydrogenolysis", 63(13): 4172-4173 (1998).
Gavhane et al., "Solid tumors: Facts, challenges, and solutions", International Journal of Pharma Sciences and Research, 2(1): 1-12 (2011).
Goodford, "A Computational Procedure for Determining Energetically Favorable Binding Sites on Biologically Important Macromolecules," J. Med. Chem., 28(7): 849-857 (1985).
Goodsell et al., "Automated Docking of Substrates to Proteins by Simulated Annealing", Proteins: Structure, Function, and Genetics, 8: 195-202 (1990).
Greer et. al., "The updated biology of hypoxia inducible factor", EMBO J. 31: 2448-2460 (2012).
Hardcastle et al., "Discovery of Potent Chromen-4-one Inhibitors of the DNA-Dependent Protein Kinase (DNA-PK) Using a Small-Molecule Library Approach", J. of Medicinal Chem., 48(24): 7829-7846 (2005).
Hoeksema et al., "Structure of Rubradirin", J. of American Chem. Society, 104(19): 5173-5181 (1982).
Hu et al., "Differential Roles of Hypoxia-Inducible Factor 1α (HIF-1α) and HIF-2α in Hypoxic Gene Regulation", Mol. Cell. Biol., 23: 9361-9374 (2003).
Ingersoll et al. "Hippuric Acid", Organic Syntheses, CV 2, 328; retrieved from the internet at <http:web.archive.org/web20020724l35719/http://orgsyn.org/orgsyn/prepContent.asp?prep=cv2p032 8> on Mar. 11, 2010.
International Preliminary Report on Patentability dated Nov. 10, 2020 for PCT/US2019/031310.
International Search Report dated Nov. 14, 2019 for PCT/US2019/031310.

(56) References Cited

OTHER PUBLICATIONS

International Union of Pure and Applied Chemistry, Glossary of Class Names of Organic Compounds and Reactive Intermediates Based on Structure, Pure & D Annl. Chem., 67(8/9): 1307-1375 (1995).
Ivan et al., "Biochemical purification and pharmacological inhibition of a mammalian prolyl hydroxylase acting on hypoxia-inducible factor," Proceedings of the National Academy of Science, 99(21): 13459-13464 (2002).
Ivan et al., "HIFα Targeted for VHL-Mediated Destruction by Proline Hydroxylation: Implications for 02 Sensing", Science, 292: 464-468 (2001).
Ivanisevic et al., "Uses of X-Ray Powder Diffraction in the Pharmaceutical Industry." Pharmaceutical Formulation & Quality. Aug./Sep. 2011: 30-33 (2011).
Iyoda et al., "Homocoupling of aryl halides using nickel(II) complex and zinc in the presence of Et4Nl. An efficient method for the synthesis of biaryls and bipyridines", Bull. Chem. Soc. Jpn., 63(1): 80-87 (1990).
Jaakkola et al., "Targeting of HIF-α to the von Rippel-Lindau Ubiquitylation Complex by O2-Regulated Prolyl Hydroxylation," Science, 292: 468-472 (2001).
Jones et al., "Molecular Recognition of Receptor Sites Using a Genetic Algorithm with a Description of Desolvation", J. Mol. Biol., 245: 43-53 (1995).
Kaelin, "Proline Hydroxylation and Gene Expression," Annual Rev. Biochem., 74: 115-125 (2005).
Karuppagounder et al., "Hypoxia-inducible factor prolyl hydroxylase inhibition: robust new target or another big bust for stroke therapeutics?", J. Cereb. Blood F. Met., 32: 1347-1361 (2012).
Kawashima et al., "Suppressive effect of quinolinic acid and hippuric acid on bone marrow erythroid growth and lymphocyte blast formation in uremia", Advances in Experimental Medicine and Biology, 223: 69-72 (1987).
Ke and Costa, "Hypoxia-Inducible Factor-I (HIF-1)", Molecular Pharmacology, 70(5): 1469-1480 (2006).
Khandhadia et al., "Neurodegenerative Diseases", edited by Shamim I. Alnned, Published by Landes Biosciences and Springer Science+Business Media, Chapter 2: 15-36 (2012).
Kietzmann et al., "Perivenous expression of the mRNA of the three hypoxia-inducible factor a-subunits, HIF1α, HIF2α and HIF3α, in rat liver", Biochem. J., 354: 531-537 (2001).
Kim et al., "Recent advances in developing inhibitors for hypoxia-inducible factor prolyl hydroxylases and their therapeutic implications", Molecules, 20: 20551-20568 (2015).
Krantz, "Erythropoietin," Blood, 77: 419-434 (1991).
Kuntz et al., "A Geometric Approach to Macromolecule-Ligand Interactions," J. Mol. Biol., 161: 269-288 (1982).
Kurti et al., "Strategic applications of named reactions in organic synthesis", El Sevior: 448-449 and 484-485 (2005).
Langsetmo et al., "Inhibition of HIF-Prolyl Hydroxylases with FG-4539 Is Neuroprotective in a Mouse Model of Permanent Focal Ischemia", International Stroke Conference, Kissimmee Florida, Presentation No. 427 (2006).
Lee et al., "Structure of Human FIH-1 Reveals a Unique Active Site Pocket and Interaction Sites for HIF-1 and von Hippel Lindau", JBC, 278: 7558-7563 (2003).
Li et al., "PR39, A Peptide Regulator of Angiogenesis," Nat Med., 6(1): 49-55 (2000).
Lima and Barreiro, "Bioisosterism: A Useful Strategy for Molecular Modification and Drug Design", Current Medicinal Chemistry, 12: 23-49 (2005).
Liu et al., "Hypoxia Induces Genomic DNA Demethylation through the Activation of HIF-1alpha and Transcriptional Upregulation of MAT2A in Hepatoma Cells", Mol. Cancer Ther., 10: 1113-1123 (Jun. 2011).
Mancini et al., "Effect of Erythropoietin on Exercise Capacity in Patients with Moderate to Severe Chronic Heart Failure", Circulation, 107: 294-299 (2003).
McDonough et al., "Cellular Oxygen Sensing: Crystal Structure of Hypoxia-Inducible Factor Prolyl Hydroxylase (PHD2)", PNAS, 103(26): 9814-9819 (2006).
Miranker et al., "Functionality Maps of Binding Sites: A Multiple Copy Simultaneous Search Method", Proteins: Structure, Function and Genetics, 11: 29-34 (1991).
Morissette et al., "High-throughput crystallization: polymorphs, salts, co-crystals and solvates of pharmaceutical solids", Advanced Drug Delivery Reviews, 56: 275-300 (2004).
Myerson, Handbook of Industrial Crystallization, p. 249 (2002).
Nguyen et al., "Cellular Interactions in Vascular Growth and Differentiation", Int. Review of Cytology, 204: 1-48 (2001).
Nielsen et. al., "Antiangiogenic therapy for Breast Cancer", Breast Cancer Res. 12: 209-227 (2010).
Nishibata et al., "Automatic Creation of Drug Candidate Structures Based on Receptor Structure. Starting Point for Artificial Lead Generation", Tetrahedron, 47(43): 8985-8990 (1991).
Nowak et al., "Age-related macular degeneration (AMD): pathogenesis and therapy", Pharmacological Reports, 58: 353-363 (2006).
O'Reilly et al., "Angiostatin: A Novel Angiogenesis Inhibitor that Mediates the Suppression of Metastases by a Lewis Lung Carcinoma", Cell, 79: 315-328 (1994).
O'Reilly et al., "Endostatin: An Endogenous Inhibitor of Angiogenesis and Tumor Growth", Cell, 88: 277-285 (1997).
Pasqualetti et al., "Circadian rhythm of serum erythropoietin in myelodysplastic syndromes", European Review for Medical and Pharmacological Sciences, 4: 111-115 (2000).
Pergola et al, "Vadadustat, a novel oral HIF stabilizer, provides effective anemia treatment in nondialysis-dependent chronic kidney disease", 90: 1115-1122 (2016).
Peyssonnaux et al., "HIF-10 Expression Regulates the Bactericidal Capacity of Phagocytes", J. Clinical Invest., 115(7): 1806-1815 (2005).
Piyamongkol et al., "Amido-3-hydroxypyridin-4-ones as Iron (III) Ligands", Chemistry A European Journal, 16: 6374-6381 (2010).
Prabhakar et al., "Adaptive and Maladaptive Cardiorespiratory Responses to Continuous and Intermittent Hypoxia Mediated by Hypoxia-Inducible Factors 1 and 2", Physiol. Rev., 92: 967-1003 (2012).
PubChem Open Chemistry Database Compound Name: SCHEMBL3484399 (CID 49848485); Retrieved on from the internet: <https://pubchem.ncbi.nlm.nih.gov/compound/49848485> on Mar. 15, 2016.
PubChem Open Chemistry Database Compound Name: ZEADCOHJERWFOI-UHFFFAOYSA-M (CID 71491828); retrieved from the internet: <https://pubchem.ncbi.nlm.nih.gov/compound/71491828> on Mar. 21, 2016.
Qian et al., "A Randomized, Double-Blind, Placebo Controlled Trial of FG-4592 for Correction of Anemia in Subjects with Chronic Kidney Disease in China," Oral Abstract FR-ORO11, J. Am. Soc. Nephrol., 24: 38A (2013).
Qunibi et al., "A randomized controlled trial comparing intravenous ferric carboxymaltose with oral iron for treatment of iron deficiency of non-dialysis-dependent chronic kidney disease patients", Nephrol Dial Transplant, 26(5): 1599-1607 (2011).
Rahtu-Korpela et al., "HIF Prolyl 4-Hydroxylase-2 inhibition improves Glucose and Lipid Metabolism and Protects Against Obesity and Metabolic Dysfunction," Diabetes 63: 3324-3333 (2014).
Rankin et al., "Hypoxia-inducible factor-2 (HIF-2) regulates hepatic erythropoietin in vivo" J. Clin. Invest. 117:1069-1076 (2007).
Ratcliffe et al., "HIF-1 and HIF-2: working alone or together in hypoxia?" J. Clin. Inv., 117(4):862-865 (2007).
Redondo et al., "Vascular endothelial growth factor (VEGF) and melanoma. N-Acetylcysteine downregulates VEGF production in vitro", Cytokine, 12(4):374-378 (2000).
Roda et al., "Stabilization of HIF-2α induces sVEGFR-1 production from tumor-associated macrophages and decreases tumor growth in a murine melanoma model", J. Immunology, 189: 3168-3177 (2012).
Schelhaas and Waldmann, "Protecting Group Strategies in Organic Synthesis", Chem. Int. Ed. Engl., 36: 2056-2083 (1996).
Schoneberg et al., "Structural Basis of G Protein-Coupled Receptor Function," Molecular and Cellular Endocrinology, 151: 181-193 (1999).

(56) References Cited

OTHER PUBLICATIONS

"Hippuric acid sodium salt", Science Lab.com: Chemicals & Laboratory Equipment; retrieved from the internet at <http://web.archive.org/web/20041107121553/http://www.sciencelab.com/page/S/PVAR/10415/SLH2620> on Mar. 11, 2010.
Semenza et al., "Regulation of Erythropoietin Production: New Insights into Molecular Mechanisms of Oxygen Homeostasis", Hematol. Oncol. Clin. North Am., 8: 863-884 (1994).
Semenza et al., "Transcriptional Regulation of Genes Encoding Glycolytic Enzymes by Hypoxia-Inducible Factor I", J. Biol. Chem., 269: 23757-23763 (1994).
Semenza, "HIF-1 and human disease: one highly involved factor", Genes & Development, 14: 1983-1991 (2000).
Semenza, "Signal Transduction to Hypoxia-inducible Factor I", Biochem. Pharmacol, 64: 993-998 (2002).
Sexton, "Recent advances in our understanding of peptide hormone receptors and RAMPS", Current Opinion in Drug Discovery and Development, 2(5): 440-448 (1999).
Seymour et al., "Decision T 0777/08 of the Boards of Appeal of the European Patent Office", retrieved from the internet: <http://www.epo.org/law-practice/case-law-appeals/pdf/1080777exl.pdf> on Dec. 19, 2017 (2011).
Sheehan, "3-Hydroxypicolinic Acid and Some of its Derivatives", J. Organic Chemistry 31(3): 636-638 (1996).
Siddiq, "Hypoxia-inducible factor prolyl 4-hydroxylase inhibition", J. of Biological Chemistry, 280(50):41732-41743 (2005).
Sowter et al., "Predominant Role of Hypoxia-Inducible Transcription Factor (Hif)-1α versus (Hif)-2α in Regulation of the Transcriptional Response to Hypoxia", Cancer Res. 63: 6130-6134 (2003).
Sporn and Suh, "Chemoprevention of cancer", Carcinogenesis, 21(3): 525-530(2000).
Stille, J. K Angew. Chern., Int. ED. Engl., vol. 25: 508 (1986).
Stohlawetz et al., "Effects of erythropoietin on platelet reactivity and thrombopoiesis in humans", Blood, 95(9): 2983-2989 (2000).
Sutter, "Hypoxia-inducible factor 1 alpha protein expression is controlled by oxygen-regulated ubiquitination that is disrupted by deletions and missense mutations", PNAS, 97(9): 4748-4753 (2000).
Teicher et al., "Potentiation of Cytotoxic Cancer Therapies by TNP-470 Alone and with Other Anti-Angiogenic Agents", Int. J. Cancer, 57: 920-925 (1994).
Thoppil and Bishayee, "Terpenoids as potential chemopreventive and therapeutic agents in liver cancer", World J. Hepatol., 3(9): 228-249 (2011).
Thornber, "Isosterism and Molecular Modification in Drug Design", Progress Drug Res., vol. 37:563-580 (1979).
Tzschucke et al., "Fluorous-Silica-Supported Perfluoro-Tagged Palladium Complexes Catalyze Suzuki Coupling in Water", Helvetica Chimica Acta; 87: 2882-2889 (2004).
Ullmann F., J. Bielecki, Ber. Deutsch. Chem. Ges. 1901, p. 2174, 34. (1901).
Variankaval et al., "From form to function: crystallization of active pharmaceutical ingredients", AICHE Journal, Jul. 2008, 54(7): 1682-1688 (2008).
Vickerstaffe et al., "Fully Automated Polymer-Assisted Synthesis of 1,5-Biaryl Pvrazoles", J. Comb. Chem., 6:332-33 (2004).
Vincent et al., "Angiogenesis is Induced in a Rabbit Model of Hindlimb Ischemia by Naked DNA Encoding an HIF-1α/VP16 Hybrid Transcription Factor", Circulation, 102: 2255-2261 (2000).
Vippagunta et al., "Crystalline solids", Adv. Drug Deliv. Rev., 48(1): 3-26 (2001).
Wade et al., "Organic Chemistry", 6th ED., Pearson Prentice Hall, US: 780-781 (2006).
Warnecke et al., "Activation of the Hypoxia-Inducible Factor Pathway and Stimulation of Angiogenesis by Application of Prolyl Hydroxylase Inhibitors", FASEB Journal, 17: 1186-1188 (2003).
Warshakoon et al., "Design and synthesis of substituted pyridine derivatives as HIF-1alpha prolyl hydroxylase inhibitors", Bioorganic & Medicinal Chemistry Letters, 16: 5616-5620 (2006).
Wax et al., "SM-20 is a Novel20-kd Protein Whose Expression in the Arterial Wall is Restricted to Smooth Muscle", Lab. Invest., 74(4): 797-808 (1996).
Weidner et al., "Tumor Angiogenesis and Metastasis—Correlation in Invasive Breast Carcinoma", New Eng. J. Med., 324(1): 1-8 (1991).
Wiesener et al., "Widespread hypoxia-inducible expression of HIF-2alpha in distinct cell populations of different organs." FASEB J. 17(2): 271-3 (2003).
Wright et al., "Activation of the Prolyl Hydroxylase Oxygen-Sensor Results in Induction of GLUTI, Heme Oxygenase-1, and Nitric-Oxide Synthase Proteins and Confers Protection from Metabolic Inhibition to Cardiomyocytes", J. Bio. Chem., 278(22): 20235-20239 (2003).
Written Opinion of the International Searching Authority dated Aug. 7, 2019 for PCT/US2019/031310.
Wu et. al., "A systems biology perspective on sVEGFR1: its biological function, pathogenic role and therapeutic use", J. Cell. Mol. Med. 14:528-552 (2010).
Yang et al., "Desmoplakin acts as a tumor suppressor by inhibition of the Wnt/beta-catenin signaling pathway in human lung cancer", Carcinogenesis, 33(10): 1863-1870 (2012).

PROCESS FOR PREPARING 2-[[5-(3-CHLOROPHENYL)-3-HYDROXYPYRIDINE-2-CARBONYL]AMINO]ACETIC ACID

CROSS-REFERENCE TO RELATED APPLICATION

The present application is a 35 U.S.C. § 371 National Stage Application of International Application No. PCT/US2019/031310, filed on May 8, 2019 which claims benefit of U.S. Provisional Application No. 62/669,135, filed May 9, 2018, each of which is hereby incorporated by reference in its entirety.

FIELD

The invention relates generally to synthetic methods and chemical compositions and more specifically to processes and intermediates thereof useful in preparation and manufacturing of vadadustat (2-[[5-(3-chlorophenyl)-3-hydroxypyridine-2-carbonyl]amino]acetic acid).

BACKGROUND

Vadadustat is a titratable, oral hypoxia-inducible factor prolyl hydroxylase inhibitor that induces endogenous erythropoietin synthesis and enhances iron mobilization. While methods for synthesis of vadadustat have been described, there remains a need for improved methods to manufacture highly pure vadadustat or a pharmaceutically acceptable salt thereof substantially free of the impurities.

SUMMARY

The present invention is based, in part, on the surprising discovery that highly pure vadadustat or a pharmaceutically acceptable salt thereof, which is substantially free of impurities can be manufactured using the methods and compositions described herein.

Disclosed herein are methods and processes of preparing vadadustat and pharmaceutically acceptable salts thereof, and intermediates and their salts useful for the synthesis of vadadustat.

In one aspect, disclosed herein is a process for preparing a compound of Formula (8),

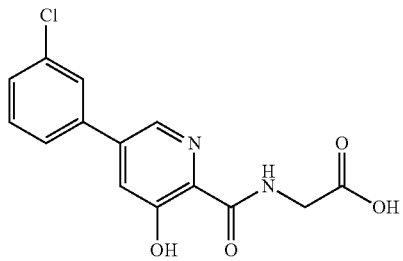

(8)

or a salt thereof, comprising: contacting a compound of Formula (I) or a salt thereof,

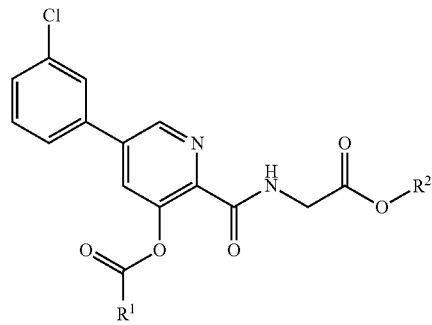

(I)

wherein: $R^1$ is $C_{1-4}$ alkyl, $CH_2Cl$, phenyl, or benzyl, in which each of phenyl and benzyl may be independently substituted with one, two or three substituents selected from methyl, methoxy, nitro and halogen; and $R^2$ is $C_{1-4}$ alkyl, with a hydrolyzing agent.

In another aspect, disclosed herein is a compound of Formula (I):

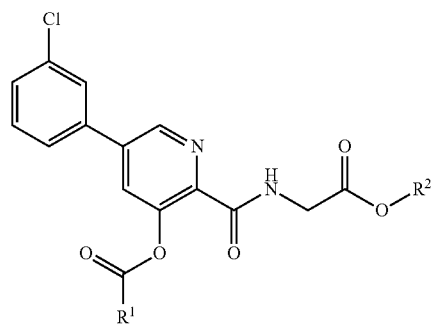

(I)

or a salt thereof, wherein: $R^1$ is $C_{1-4}$ alkyl, $CH_2Cl$, phenyl, or benzyl, in which each of phenyl and benzyl may be independently substituted with one, two or three substituents selected from methyl, methoxy, nitro and halogen; and $R^2$ is $C_{1-4}$ alkyl.

In another aspect, disclosed herein is a composition comprising:
a) 80% or more of a compound of Formula (I) or a salt thereof,

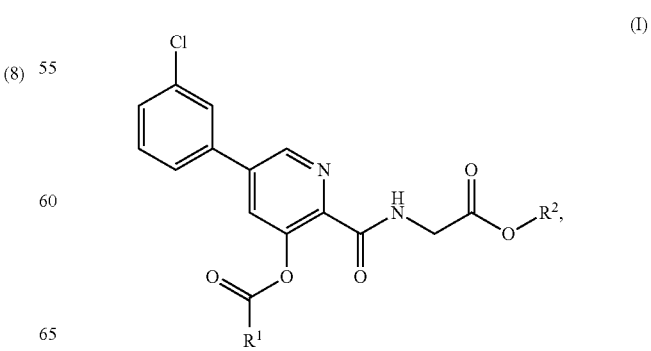

(I)

wherein each of R¹ and R² is independently as defined herein; and b) 20% or less of a compound of Formula (IV) or a salt thereof,

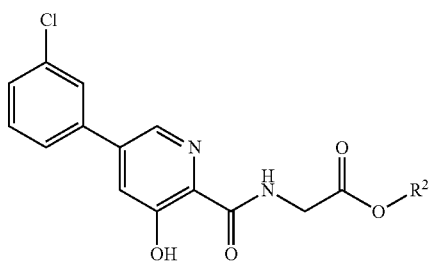

(IV)

wherein R² is as defined herein, and wherein the combined amount of the compound of Formula (I) or a salt thereof and the compound of Formula (IV) or a salt thereof is between about 99% and about 100%.

DETAILED DESCRIPTION

The materials, compounds, compositions, articles, and methods described herein may be understood more readily by reference to the following detailed description of specific aspects of the disclosed subject matter and the Examples included therein.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

All temperatures are in degrees Celsius (° C.) unless otherwise specified.

Unless noted otherwise, all purity and related numeric values (%) are as measured by HPLC.

As used herein and in the appended claims, the singular forms "a," "and," and "the" include plural referents unless the context clearly dictates otherwise. Thus, for example, reference to "a compound" includes a plurality of such agents, and reference to "the salt" includes reference to one or more salts (or to a plurality of salts) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range.

As used in the specification and appended claims, unless specified to the contrary, the following terms have the meaning indicated below.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

The compounds disclosed herein may contain one or more asymmetric centers and may thus give rise to enantiomers, diastereomers, and other stereoisomeric forms that may be defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

"Amino" refers to the —NH₂ radical.

"Alkyl" refers to a straight or branched hydrocarbon chain radical consisting solely of carbon and hydrogen atoms, containing no unsaturation, having from one to fifteen carbon atoms (e.g., $C_{1-15}$ alkyl). In certain embodiments, an alkyl comprises one to thirteen carbon atoms (e.g., $C_{1-13}$ alkyl). In certain embodiments, an alkyl comprises one to ten carbon atoms (e.g., $C_{1-10}$ alkyl). In certain embodiments, an alkyl comprises one to eight carbon atoms (e.g., $C_{1-8}$ alkyl). In other embodiments, an alkyl comprises one to five carbon atoms (e.g., $C_{1-5}$ alkyl). In other embodiments, an alkyl comprises one to four carbon atoms (e.g., $C_{1-4}$ alkyl). In other embodiments, an alkyl comprises one to three carbon atoms (e.g., $C_{1-3}$ alkyl). In other embodiments, an alkyl comprises one to two carbon atoms (e.g., $C_{1-2}$ alkyl). In other embodiments, an alkyl comprises one carbon atom (e.g., $C_1$ alkyl). In other embodiments, an alkyl comprises five to fifteen carbon atoms (e.g., $C_{5-15}$ alkyl). In other embodiments, an alkyl comprises five to ten carbon atoms (e.g., $C_{5-10}$ alkyl). In other embodiments, an alkyl comprises five to eight carbon atoms (e.g., $C_{5-8}$ alkyl). In other embodiments, an alkyl comprises two to five carbon atoms (e.g., $C_{2-5}$ alkyl). In other embodiments, an alkyl comprises three to five carbon atoms (e.g., $C_{3-5}$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Halo" or "halogen" refers to bromo, chloro, fluoro or iodo substituents.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

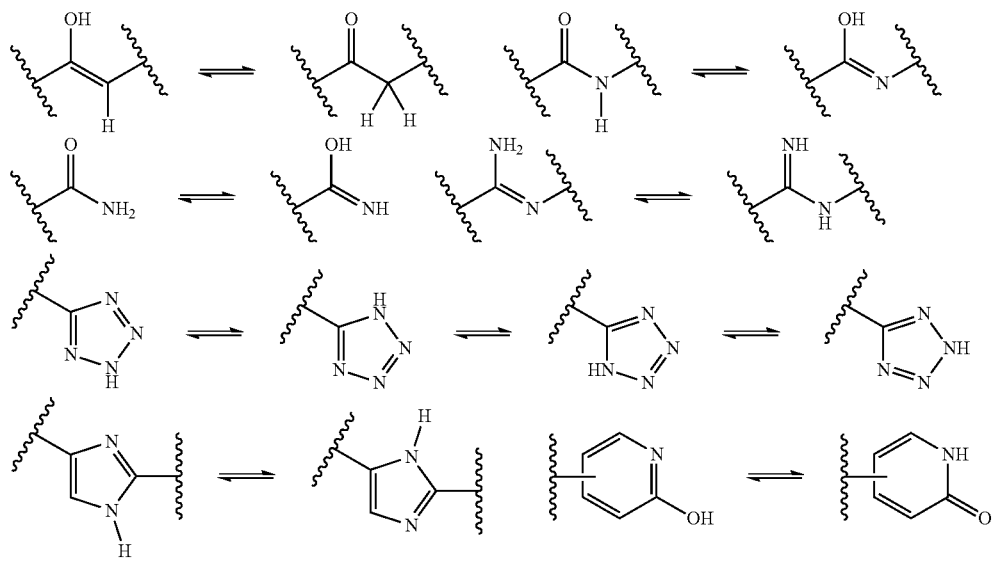

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Exemplary pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds of the present invention, whether radioactive or not, are encompassed within the scope of the present invention.

In certain embodiments, the compounds disclosed herein have some or all of the $^1$H atoms replaced with $^2$H atoms. The methods of synthesis for deuterium-containing substituted heterocyclic derivative compounds are known in the art and include, by way of non-limiting example only, the following synthetic methods.

"Protecting group" refers to a group of atoms that mask, reduce or prevent the reactivity of the functional group when attached to a reactive functional group in a molecule. Typically, a protecting group may be selectively removed as desired during the course of a synthesis. Examples of protecting groups can be found in Wuts, "Greene's Protective Groups in Organic Synthesis," 5th Ed., Wiley (2014), and Harrison et al., Compendium of Synthetic Organic Methods, Vols. 1-8, 1971-1996, John Wiley & Sons, NY. Functional groups that can have a protecting group include, but are not limited to, hydroxy, amino, and carboxy groups. Representative amine protecting groups include, but are not limited to, formyl, acetyl (Ac), trifluoroacetyl, benzyl (Bn), benzoyl (Bz), carbamate, benzyloxycarbonyl ("CBZ"), p-methoxybenzyl carbonyl (Moz or MeOZ), tertbutoxycarbonyl ("Boc"), trimethylsilyl ("TMS"), 2-trimethylsilyl-ethanesulfonyl ("SES"), trityl and substituted trityl groups, allyloxycarbonyl, 9-fiuorenylmethyloxycarbonyl ("FMOC"), nitro-veratryloxycarbonyl ("NVOC"), p-methoxybenzyl (PMB), tosyl (Ts) and the like.

"Solvate" can include, but is not limited to, a solvate that retains one or more of the activities and/or properties of the compound and that is not undesirable. Examples of solvates include, but are not limited to, a compound in combination with water, isopropanol, ethanol, methanol, DMSO, ethyl acetate, acetic acid, ethanolamine, or combinations thereof.

"Salt" can include, but are not limited to, salts that retain one or more of the activities and properties of the free acids and bases and that are not undesirable. Illustrative examples of salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, and mandelates.

"Solvent" can include, but is not limited to, non-polar, polar aprotic, and polar protic solvents. Illustrative examples of non-polar solvents include, but are not limited to, pentane, cyclopentane, hexane, cyclohexane, benzene, toluene, 1,4-dioxane, chloroform, diethyl ether, and dichloromethane (DCM). Illustrative examples of polar aprotic solvents include, but are not limited to, tetrahydrofuran (THF), ethyl acetate, acetone, dimethylformamide (DMF), acetonitrile (MeCN), dimethyl sulfoxide (DMSO), nitromethane, and propylene carbonate. Illustrative examples of polar protic solvents include, but are not limited to, formic acid, n-butanol, isopropanol (IPA), n-propanol, ethanol, methanol, acetic acid, and water.

"Acid" refers to molecules or ions capable of donating a hydron (proton or hydrogen ion H+), or, alternatively, capable of forming a covalent bond with an electron pair (e.g., a Lewis acid). Acids can include, but is not limited to, mineral acids, sulfonic acids, carboxylic acids, halogenated carboxylic acids, vinylogous carboxylic acids, and nucleic acids. Illustrative examples of mineral acids include, but are not limited to, hydrogen halides and their solutions: hydrofluoric acid (HF), hydrochloric acid (HCl), hydrobromic acid (HBr), hydroiodic acid (HI); halogen oxoacids: hypochlorous acid (HClO), chlorous acid (HClO$_2$), chloric acid (HClO$_3$), perchloric acid (HClO$_4$), and corresponding analogs for bromine and iodine, and hypofluorous acid (HFO); sulfuric acid (H$_2$SO$_4$); fluorosulfuric acid (HSO$_3$F); nitric acid (HNO$_3$); phosphoric acid (H$_3$PO$_4$); fluoroantimonic acid (HSbF$_6$); fluoroboric acid (HBF$_4$); hexafluorophosphoric acid (HPF$_6$); chromic acid (H$_2$CrO$_4$); and boric acid (H$_3$BO$_3$). Illustrative examples of sulfonic acids include, but are not limited to, methanesulfonic acid (or mesylic acid, CH$_3$SO$_3$H), ethanesulfonic acid (or esylic acid, CH$_3$CH$_2$SO$_3$H), benzenesulfonic acid (or besylic acid, C$_6$H$_5$SO$_3$H), p-toluenesulfonic acid (or tosylic acid, CH$_3$C$_6$H$_4$SO$_3$H), trifluoromethanesulfonic acid (or triflic acid, CF$_3$SO$_3$H), and polystyrene sulfonic acid (sulfonated polystyrene, [CH$_2$CH(C$_6$H$_4$)SO$_3$H]n). Illustrative examples of carboxylic acids include, but are not limited to, acetic acid (CH$_3$COOH), citric acid (C$_6$H$_8$O$_7$), formic acid (HCOOH), gluconic acid (HOCH$_2$—(CHOH)$_4$—COOH), lactic acid (CH$_3$—CHOH—COOH), oxalic acid (HOOC—COOH), and tartaric acid (HOOC—CHOH—CHOH—COOH). Illustrative examples of halogenated carboxylic acids include, but are not limited to, fluoroacetic acid, trifluoroacetic acid, chloroacetic acid, dichloroacetic acid, and trichloroacetic acid. Illustrative examples of vinylogous carboxylic acids include, but are not limited to, ascorbic acid. Illustrative examples of nucleic acids include, but are not limited to, deoxyribonucleic acid (DNA) and ribonucleic acid (RNA).

"Base" refers to molecules or ions capable of accepting protons from a proton donor and/or produce hydroxide ions (OH$^-$). Illustrative examples of bases include, but are not limited to, aluminum hydroxide (Al(OH)$_3$), ammonium hydroxide (NH$_4$OH), arsenic hydroxide (As(OH)$_3$), barium hydroxide (Ba(OH)$_2$), beryllium hydroxide (Be(OH)$_2$), bismuth(III) hydroxide (Bi(OH)$_3$), boron hydroxide (B(OH)$_3$), cadmium hydroxide (Cd(OH)$_2$), calcium hydroxide (Ca(OH)$_2$), cerium(III) hydroxide (Ce(OH)$_3$), cesium hydroxide (CsOH), chromium(II) hydroxide (Cr(OH)$_2$), chromium(III) hydroxide (Cr(OH)$_3$), chromium(V) hydroxide (Cr(OH)$_5$), chromium(VI) hydroxide (Cr(OH)$_6$), cobalt(II) hydroxide (Co(OH)$_2$), cobalt(III) hydroxide (Co(OH)$_3$), copper(I) hydroxide (CuOH), copper(II) hydroxide (Cu(OH)$_2$), gallium(II) hydroxide (Ga(OH)$_2$), gallium(III) hydroxide (Ga(OH)$_3$), gold(I) hydroxide (AuOH), gold(III) hydroxide (Au(OH)$_3$), indium(I) hydroxide (InOH), indium(II) hydroxide (In(OH)$_2$), indium(III) hydroxide (In(OH)$_3$), iridium(III) hydroxide (Ir(OH)$_3$), iron(II) hydroxide (Fe(OH)$_2$), iron(III) hydroxide (Fe(OH)$_3$), lanthanum hydroxide (La(OH), lead (II) hydroxide (Pb(OH)$_2$), lead(IV) hydroxide (Pb(OH)$_4$), lithium hydroxide (LiOH), magnesium hydroxide (Mg(OH)$_2$), manganese(II) hydroxide (Mn(OH)$_2$), manganese(III) hydroxide (Mn(OH)$_3$), manganese(IV) hydroxide (Mn(OH)$_4$), manganese(VII) hydroxide (Mn(OH)$_7$), mercury(I) hydroxide (Hg$_2$(OH)$_2$), mercury(II) hydroxide (Hg(OH)$_2$), molybdenum hydroxide (Mo(OH)$_3$), neodymium hydroxide (Nd(OH)$_3$), nickel oxo-hydroxide (NiOOH), nickel(II) hydroxide (Ni(OH)$_2$), nickel(III) hydroxide (Ni(OH)$_3$), niobium hydroxide (Nb(OH)$_3$), osmium(IV) hydroxide (Os(OH)$_4$), palladium(II) hydroxide (Pd(OH)$_2$), palladium(IV) hydroxide (Pd(OH)$_4$), platinum(II) hydroxide (Pt(OH)$_2$), platinum(IV) hydroxide (Pt(OH)$_4$), plutonium(IV) hydroxide (Pu(OH)$_4$), potassium hydroxide (KOH), radium hydroxide (Ra(OH)$_2$), rubidium hydroxide (RbOH), ruthenium(III) hydroxide (Ru(OH)$_3$), scandium hydroxide (Sc(OH)$_3$), silicon hydroxide (Si(OH)$_4$), silver hydroxide (AgOH), sodium hydroxide (NaOH), strontium hydroxide (Sr(OH)$_2$), tantalum(V) hydroxide (Ta(OH)$_5$), technetium (II) hydroxide (Tc(OH)$_2$), tetramethylammonium hydroxide (C$_4$H$_{12}$NOH), thallium(I) hydroxide (TlOH), thallium(III) hydroxide (T(OH)$_3$), thorium hydroxide (Th(OH)$_4$), tin(II) hydroxide (Sn(OH)$_2$), tin(IV) hydroxide (Sn(OH)$_4$), titanium(II) hydroxide (Ti(OH)$_2$), titanium(III) hydroxide (Ti(OH)$_3$), titanium(IV) hydroxide (Ti(OH)$_4$), tungsten(II) hydroxide (W(OH)$_2$), uranyl hydroxide ((UO$_2$)$_2$(OH)$_4$), vanadium(II) hydroxide (V(OH)$_2$), vanadium(III) hydroxide (V(OH)$_3$), vanadium(V) hydroxide (V(OH)$_5$), ytterbium hydroxide (Yb(OH)$_3$), yttrium hydroxide (Y(OH)$_3$), zinc hydroxide (Zn(OH)$_2$), and zirconium hydroxide (Zr(OH)$_4$).

In certain embodiments, the processes disclosed herein can take place concurrently, in a sequential order as described herein, or in any possible order thereof.

In one aspect, disclosed herein is a process for preparing a compound of Formula (8),

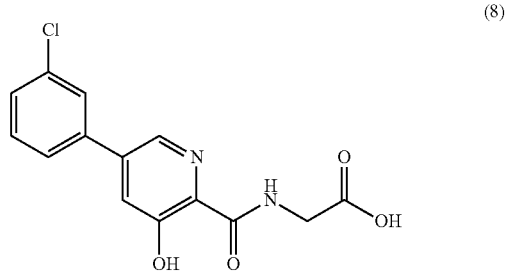

(8)

or a salt thereof, comprising: contacting a compound of Formula (I) or a salt thereof,

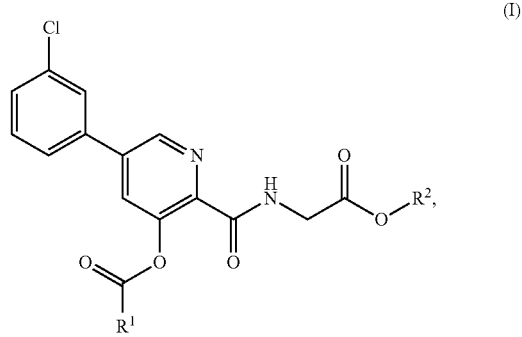

(I)

wherein R$^1$ is C$_{1-4}$ alkyl, CH$_2$Cl, phenyl, or benzyl, in which each of phenyl and benzyl may be independently substituted with one, two or three substituents selected from methyl, methoxy, nitro and halogen; and R$^2$ is C$_{1-4}$ alkyl, with a hydrolyzing agent.

In some embodiments, R$^1$ is C$_{1-4}$ alkyl, CH$_2$Cl, phenyl, or benzyl, in which each of phenyl and benzyl may be independently substituted with one or two substituents selected from methyl, methoxy, nitro and halogen. In some embodiments, R$^1$ is C$_{1-4}$ alkyl, CH$_2$Cl, phenyl, or benzyl, in which each of phenyl and benzyl may be independently substituted with one or two substituents selected from methyl, methoxy, and halogen. In some embodiments, R$^1$ is C$_{1-4}$ alkyl, CH$_2$Cl, phenyl, or benzyl, in which each of phenyl and benzyl may be independently substituted with one or two substituents selected from methoxy and halogen. In some embodiments, $R^1$ is $C_{1-4}$ alkyl, $CH_2Cl$, phenyl, or benzyl, in which each of phenyl and benzyl may be independently substituted with one or two methoxy substituents. In some embodiments, $R^1$ is $C_{1-4}$ alkyl, $CH_2Cl$, phenyl, or benzyl. In some embodiments, $R^1$ is $C_{1-4}$ alkyl, or $CH_2Cl$. In some embodiments, $R^1$ is $C_{1-4}$ alkyl. In some embodiments, $R^1$ is t-butyl.

In some embodiments, $R^2$ is a protecting group, methyl, ethyl, propyl, isopropyl, butyl, sec-butyl, isobutyl, or tert-butyl. In some embodiments, $R^2$ is methyl, ethyl, or tert-butyl. In some embodiments, $R^2$ is methyl or tert-butyl. In some embodiments, $R^2$ is tert-butyl. In some embodiments, $R^2$ is methyl.

In some embodiments, $R^1$ is $C_{1-4}$ alkyl, $CH_2Cl$, phenyl, or benzyl, and $R^2$ is methyl, ethyl, propyl, isopropyl, butyl, sec-butyl, isobutyl, or tert-butyl. In some embodiments, $R^1$ is $C_{1-4}$ alkyl, or benzyl, and $R^2$ is methyl, ethyl, or tert-butyl. In some embodiments, $R^1$ is $C_{1-4}$ alkyl, and $R^2$ is methyl or ethyl. In some embodiments, $R^1$ tert-butyl and $R^2$ is methyl.

In some embodiments, $R^1$ is a protecting group, methylbenzene, 1,2-dimethylbenzene, 1,3-dimethylbenzene, 1,4-dimethylbenzene, 1,2,3-trimethylbenzene, 1,2,4-trimethylbenzene, 1,3,5-trimethylbenzene, methoxybenzene, 1,2-dimethoxylbenzne, 1,3-dimethoxybenzne, 1,4-dimethoxybenzene, 1,2,3-trimethoxybenzene, 1,2,4-methoxylbenzene, 1,3,5-trimethoxybenzene, nitrobenzene, 1,2-dinitrobenzne, 1,3-dinitrobenzne, 1,4-dinitrobenzene, 1,2,3-trinitrobenzene, 1,2,4-nitrobenzene, 1,3,5-trinitrobenzene, fluorobenzene, 1,2-difluorobenzne, 1,3-difluorobenzne, 1,4-difluorobenzene, 1,2,3-trifluorobenzene, 1,2,4-fluorobenzene, 1,3,5-trifluorobenzene, chlorobenzene, 1,2-dichlorobenzne, 1,3-dichlorobenzne, 1,4-dichlorobenzene, 1,2,3-trichlorobenzene, 1,2,4-trichlorobenzene, 1,3,5-trichlorobenzene, bromobenzene, 1,2-dibromobenzne, 1,3-dibromobenzne, 1,4-dibromobenzene, 1,2,3-tribromobenzene, 1,2,4-tribromobenzene, 1,3,5-tribromobenzene, iodobenzene, 1,2-diiodobenzene, 1,3-diiodobenzene, 1,4-diiodobenzene, 1,2,3-triiodobenzene, 1,2,4-triiodobenzene, 1,3,5-triiodobenzene, 2-methylbenzyl, 3-methylbenzyl, 4-methylbenzyl, 2,3-dimethylbenzyl, 2,4-dimethylbenzyl, 2,5-dimethylbenzyl, 2,6-dimethylbenzyl, 3,4-dimethylbenzyl, 3,5-dimethylbenzyl, 2,3-dimethoxybenzyl, 2,4-dimethoxybenzyl, 2,5-dimethoxybenzyl, 2,6-dimethoxybenzyl, 3,4-dimethoxybenzyl, 3,5-dimethoxybenzyl, 2,3-dinitrobenzyl, 2,4-dinitrobenzyl, 2,5-dinitrobenzyl, 2,6-dinitrobenzyl, 3,4-dinitrobenzyl, 3,5-dinitrobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, 2,3-dichlorobenzyl, 2,4-dichlorobenzyl, 2,5-dichlorobenzyl, 2,6-dichlorobenzyl, 3,4-dichlorobenzyl, 3,5-dichlorobenzyl, 2,3-dibromobenzyl, 2,4-dibromobenzyl, 2,5-dibromobenzyl, 2,6-dibromobenzyl, 3,4-dibromobenzyl, 3,5-dibromobenzyl, 2,3-diiodobenzyl, 2,4-diiodobenzyl, 2,5-diiodobenzyl, 2,6-diiodobenzyl, 3,4-diiodobenzyl, or 3,5-diiodobenzyl.

In some embodiments, $R^2$ is $C_1$-$C_{12}$ linear, $C_3$-$C_{12}$ branched or $C_3$-$C_{12}$ cyclic alkyl; $C_2$-$C_{12}$ linear, $C_3$-$C_{12}$ branched or $C_3$-$C_{12}$ cyclic alkenyl; or $C_2$-$C_{12}$ linear, $C_3$-$C_{12}$ branched or $C_3$-$C_{12}$ cyclic alkynyl, or benzyl. In some embodiments, $R^2$ is $C_1$-$C_{12}$ linear, or $C_3$-$C_{12}$ branched alkenyl; $C_2$-$C_{12}$ linear, $C_3$-$C_{12}$ or branched alkenyl; $C_2$-$C_{12}$ linear, or $C_3$-$C_{12}$ alkynyl, or benzyl. In some embodiments, $R^2$ is $C_1$-$C_{12}$ linear alkenyl; $C_2$-$C_{12}$ linear alkenyl; or $C_2$-$C_{12}$ linear alkynyl, or benzyl. In some embodiments, $R^2$ is $C_1$-$C_{12}$ linear alkenyl; $C_2$-$C_{12}$ linear alkenyl; or benzyl. In some embodiments, $R^2$ is $C_1$-$C_{12}$ linear alkenyl or benzyl. In some embodiments, $R^2$ is $C_1$-$C_{12}$ linear alkenyl.

In some embodiments, the hydrolyzing agent comprises an acid. In some embodiments, the acid is formic acid, acetic acid, propionic acid, butyric acid, valeric acid, caproic acid, oxalic acid, lactic acid, malic acid, citric acid, benzoic acid, carbonic acid, uric acid, taurine, p-toluenesulfonic acid, trifluoromethanesulfonic acid, aminomethylphosphonic acid, trifluoroacetic acid (TFA), phosphonic acid, sulfuric acid, nitric acid, phosphoric acid, hydrochloric acid, ethane sulfonic acid (ESA), or any combination thereof. In some embodiments, the acid is acetic acid, p-toluenesulfonic acid, trifluoromethanesulfonic acid, trifluoroacetic acid (TFA), sulfuric acid, or hydrochloric acid. In some embodiments, the acid is trifluoroacetic acid (TFA) or hydrochloric acid. In some embodiments, the acid is hydrochloric acid.

In some embodiments, the hydrolyzing agent comprises a base. In some embodiments, the base is an alkali metal hydroxide, alkali metal carbonate, Polymer-SK (see, e.g., MacCoss et al., Synlett, 675, 2004), or tetrabutylammonium fluoride (TBAF) (see, e.g., Ren et al., J. Am. Chem. Soc., 129, 5381, 2007). In some embodiments, the base is an alkali metal hydroxide, or tetrabutylammonium fluoride (TBAF). In some embodiments, the base is an alkali metal hydroxide. In some embodiments, the base is lithium hydroxide (LiOH), sodium hydroxide (NaOH), potassium hydroxide (KOH), or cesium hydroxide (CsOH), and any combination thereof. In some embodiments, the base is sodium hydroxide (NaOH) or potassium hydroxide (KOH). In some embodiments, the base is potassium hydroxide (KOH). In some embodiments, the base is an alkali metal carbonate. In some embodiments, the base is lithium carbonate ($Li_2CO_3$), sodium carbonate ($Na_2CO_3$), potassium carbonate ($K_2CO_3$), cesium carbonate ($Cs_2CO_3$), and any combination thereof. In some embodiments, the base is potassium carbonate ($K_2CO_3$) or cesium carbonate ($Cs_2CO_3$). In some embodiments, the base is cesium carbonate ($Cs_2CO_3$).

In some embodiments, the contacting occurs in presence of a solvent. In some embodiments, the solvent comprises N,N-dimethylformide (DMF), t-butanol, dimethoxyethane (DME), acetonitrile, dichloromethane (DCM), tetrahydrofuran (THF), 2-methyltetrahydrofuran (ME-THF), isopropyl alcohol, methanol, ethanol, or any combination thereof. In some embodiments, the solvent comprises THF. In some embodiments, the solvent comprises N,N-dimethylformide (DMF), dimethoxyethane (DME), tetrahydrofuran (THF), or 2-methyltetrahydrofuran (ME-THF). In some embodiments, the solvent comprises 2-methyltetrahydrofuran (ME-THF).

In some embodiments, the purity of the compound of Formula (8) is at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of the compound of Formula (8) is at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of the compound of Formula (8) is at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of the compound of Formula (8) is at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of the compound of Formula (8) is at least 99%.

In some embodiments, disclosed herein is a process for preparing a compound of Formula (I),

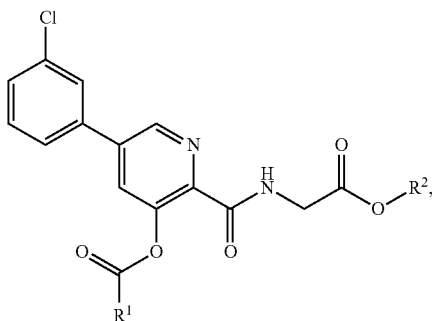

comprising:

a) contacting the compound of Formula (5) or a salt thereof,

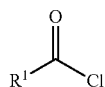

with a compound of Formula (II) or a salt thereof in the presence of a base,

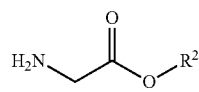

wherein $R^1$ is $C_{1-4}$ alkyl, $CH_2Cl$, phenyl, or benzyl, in which each of phenyl and benzyl may be independently substituted with one, two or three substituents selected from methyl, methoxy, nitro and halogen;

b) contacting a product formed in step a) with a compound of Formula (III) or a salt thereof in the presence of a base, (III)

wherein $R^2$ is $C_{1-4}$ alkyl;

to provide the compound of Formula (I) or a salt thereof,

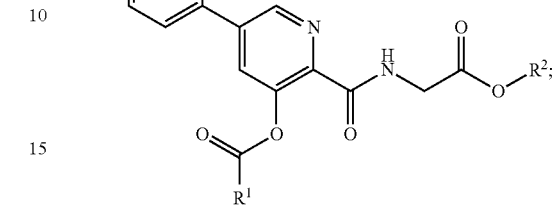

and c) optionally washing a product formed in step b) with a solvent comprising water and base.

In some embodiments, a small amount of a compound of Formula (IV) may be formed after step b) or step c). The compound of Formula (I) along with the compound of Formula (IV) can be converted directly to the compound of Formula (8) via hydrolysis as described herein.

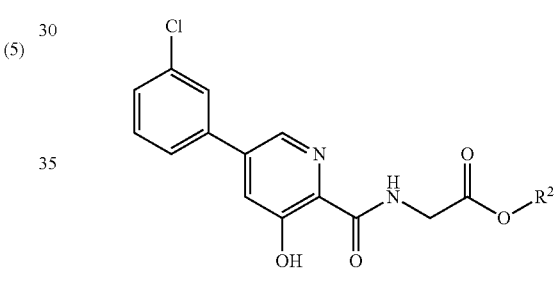

In some embodiments, $R^1$ is $C_{1-4}$ alkyl, $CH_2Cl$, phenyl, or benzyl, in which each of phenyl and benzyl may be independently substituted with one or two substituents selected from methyl, methoxy, nitro and halogen. In some embodiments, $R^1$ is $C_{1-4}$ alkyl, $CH_2Cl$, phenyl, or benzyl, in which each of phenyl and benzyl may be independently substituted with one or two substituents selected from methyl, methoxy, and halogen. In some embodiments, $R^1$ is $C_{1-4}$ alkyl, $CH_2Cl$, phenyl, or benzyl, in which each of phenyl and benzyl may be independently substituted with one or two substituents selected from methoxy and halogen. In some embodiments, $R^1$ is $C_{1-4}$ alkyl, $CH_2Cl$, phenyl, or benzyl, in which each of phenyl and benzyl may be independently substituted with one or two methoxy substituents. In some embodiments, $R^1$ is $C_{1-4}$ alkyl, $CH_2Cl$, phenyl, or benzyl. In some embodiments, $R^1$ is $C_{1-4}$ alkyl, or $CH_2Cl$. In some embodiments, $R^1$ is $C_{1-4}$ alkyl. In some embodiments, $R^1$ is t-butyl.

In some embodiments, $R^2$ is a protecting group, methyl, ethyl, propyl, isopropyl, butyl, sec-butyl, isobutyl, or tert-butyl. In some embodiments, $R^2$ is methyl, ethyl, or tert-butyl. In some embodiments, $R^2$ is methyl or tert-butyl. In some embodiments, $R^2$ is methyl. In some embodiments, $R^1$ is t-butyl, and $R^2$ is methyl.

In some embodiments, the contacting occurs in presence of a base. In some embodiments, the base is independently an organic base. In some embodiments, the organic base is triethylamine (TEA), triisopropylamine, diisopropylamine (DIPEA), pyridine, 2,6-Di-tert-butylpyridine, 1,8-Diazabicycloundec-7-ene (DBU), 1,5-Diazabicyclo(4.3.0)non-5-ene (DBN), or any combination thereof. In some embodiments, the organic base is triethylamine (TEA), diisopropylamine (DIPEA), pyridine, or 1,8-Diazabicycloundec-7-ene (DBU). In some embodiments, the organic base is triethylamine (TEA) or diisopropylamine (DIPEA). In some embodiments, the organic base is diisopropylamine (DIPEA).

In some embodiments, the contacting occurs in presence of a solvent. In some embodiments, the solvent comprises ethanol, N,N-dimethylformide (DMF), diethylformamide (DEF), dimethylacetamide (DMA), diethylacetamide (DEA), dimethyl sulfoxide(DMSO), dioxane, dimethoxyethane (DME), acetonitrile, dichloromethane (DCM), tetrahydrofuran (THF), 2-methyltetrahydrofuran (ME-THF), or any combination thereof. In some embodiments, the solvent comprises ethanol, N,N-dimethylformide (DMF), dimethylacetamide (DMA), dimethyl sulfoxide(DMSO), dichloromethane (DCM), tetrahydrofuran (THF), or 2-methyltetrahydrofuran (ME-THF). In some embodiments, the solvent comprises N,N-dimethylformide (DMF), tetrahydrofuran (THF), or 2-methyltetrahydrofuran (ME-THF). In some embodiments, the solvent comprises N,N-dimethylformide (DMF) or tetrahydrofuran (THF). In some embodiments, the solvent comprises tetrahydrofuran (THF).

In some embodiments, step c) is required. In some embodiments, the product formed in step c) comprises less than about 0.5% of the compound of Formula (5). In some embodiments, the product formed in step c) comprises less than about 0.4% of the compound of Formula (5). In some embodiments, the product formed in step c) comprises less than about 0.3% of the compound of Formula (5). In some embodiments, the product formed in step c) comprises less than about 0.2% of the compound of Formula (5). In some embodiments, the product formed in step c) comprises less than about 0.1% of the compound of Formula (5). In some embodiments, the product formed in step c) comprises less than about 0.09% of the compound of Formula (5). In some embodiments, the product formed in step c) comprises less than about 0.08% of the compound of Formula (5). In some embodiments, the product formed in step c) comprises less than about 0.07% of the compound of Formula (5). In some embodiments, the product formed in step c) comprises less than about 0.06% of the compound of Formula (5). In some embodiments, the product formed in step c) comprises less than about 0.05% of the compound of Formula (5). In some embodiments, the product formed in step c) comprises less than about 0.04% of the compound of Formula (5). In some embodiments, the product formed in step c) comprises less than about 0.03% of the compound of Formula (5). In some embodiments, the product formed in step c) comprises less than about 0.02% of the compound of Formula (5). In some embodiments, the product formed in step c) comprises less than about 0.01% of the compound of Formula (5).

In some embodiments, the solvent used in step c) comprises water and a base. In some embodiments, the water to base ratio (v/v) is about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, or about 95%-99%. In some embodiments, the base is an organic base. In some embodiments, the organic base is triethylamine (TEA), triisopropylamine, diisopropylamine (DIPEA), pyridine, 2,6-Di-tert-butylpyridine, 1,8-Diazabicycloundec-7-ene (DBU), 1,5-Diazabicyclo(4.3.0)non-5-ene (DBN), or any combination thereof. In some embodiments, the organic base is triethylamine (TEA), diisopropylamine (DIPEA), pyridine, or 1,8-Diazabicycloundec-7-ene (DBU). In some embodiments, the organic base is triethylamine (TEA) or diisopropylamine (DIPEA). In some embodiments, the organic base is diisopropylamine (DIPEA).

In another aspect, disclosed herein is a compound of Formula (I):

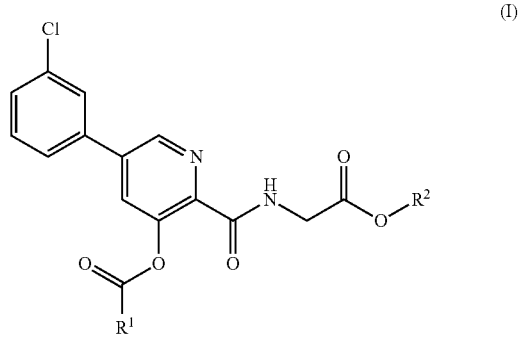

or a salt thereof, wherein $R^1$ is $C_{1-4}$ alkyl, $CH_2Cl$, phenyl, or benzyl, in which each of phenyl and benzyl may be independently substituted with one, two or three substituents selected from methyl, methoxy, nitro and halogen; and $R^2$ is $C_{1-4}$ alkyl.

In some embodiments, the purity of the compound of Formula (I) is at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of compound of Formula (I) is at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of the compound of Formula (I) is at least at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of the compound of Formula (I) is at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of the compound of Formula (I) is at least 99%.

In some embodiments, the compound of Formula (I) comprises less than about 0.5% of the compound of Formula (5), i.e., the compound of Formula (I) contains less than about 0.5% of an impurity that is the compound of Formula (5). Throughout the claims and specification, the sentence of "the compound of Formula (I) comprises less than about X % of the compound of Formula (5)" means that the compound of Formula (I) contains less than about X % of an impurity that is the compound of Formula (5). In some embodiments, the compound of Formula (I) comprises less than about 0.4% of the compound of Formula (5). In some embodiments, the compound of Formula (I) comprises less than about 0.3% of the compound of Formula (5). In some embodiments, the compound of Formula (I) comprises less than about 0.2% of the compound of Formula (5). In some embodiments, the compound of Formula (I) comprises less than about 0.1% of the compound of Formula (5). In some embodiments, the compound of Formula (I) comprises less than about 0.09% of the compound of Formula (5). In some embodiments, the compound of Formula (I) comprises less than about 0.08% of the compound of Formula (5). In some embodiments, the compound of Formula (I) comprises less than about 0.07% of the compound of Formula (5). In some embodiments, the compound of Formula (I) comprises less than about 0.06% of the compound of Formula (5). In some embodiments, the compound of Formula (I) comprises less than about 0.05% of the compound of Formula (5). In some embodiments, the compound of Formula (I) comprises less than about 0.04% of the compound of Formula (5). In some embodiments, the compound of Formula (I) comprises less than about 0.03% of the compound of Formula (5). In some embodiments, the compound of Formula (I) comprises less than about 0.02% of the compound of Formula (5). In some embodiments, the compound of Formula (I) comprises less than about 0.01% of the compound of Formula (5).

In another aspect, disclosed herein is a composition comprising:
a) 80% or more of a compound of Formula (I) or a salt thereof,

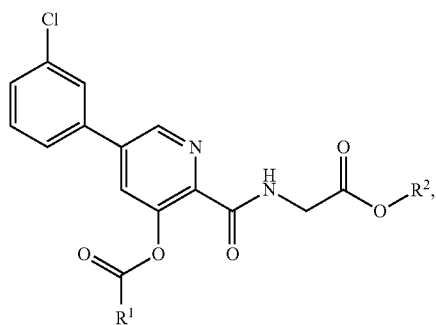

(I)

wherein $R^1$ is $C_{1-4}$ alkyl, $CH_2Cl$, phenyl, or benzyl, in which each of phenyl and benzyl may be independently substituted with one, two or three substituents selected from methyl, methoxy, nitro and halogen; and $R^2$ is $C_{1-4}$ alkyl;
b) 20% or less of a compound of Formula (IV) or a salt thereof,

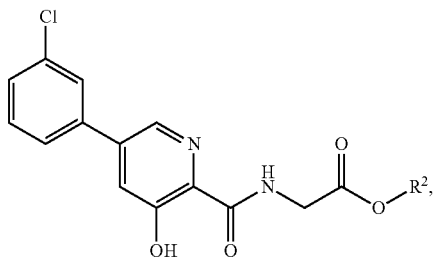

(IV)

wherein $R^2$ is $C_{1-4}$ alkyl, and wherein the combined amount of the compound of Formula (I) or a salt thereof and the compound of Formula (IV) or a salt thereof is between about 99% and about 100%, for example, at about 99.1%, about 99.2%, about 99.3%, about 99.4%, about 99.5%, about 99.6%, about 99.7%, about 99.8%, or about 99.9%.

In some embodiments, $R^2$ is a protecting group, methyl, ethyl, propyl, isopropyl, butyl, sec-butyl, isobutyl, or tert-butyl. In some embodiments, $R^2$ is methyl, ethyl, or tert-butyl. In some embodiments, $R^2$ is methyl or tert-butyl. In some embodiments, $R^2$ is methyl.

In some embodiments, the composition comprises about 85% or more of a compound of Formula (I) or a salt thereof and about 15% or less of the compound of Formula (IV) or a salt thereof. In some embodiments, the composition comprises about 90% or more of a compound of Formula (I) or a salt thereof and about 10% or less of the compound of Formula (IV) or a salt thereof. In some embodiments, the composition comprises about 95% or more of a compound of Formula (I) or a salt thereof and about 5% or less of the compound of Formula (IV) or a salt thereof. In some embodiments, the composition comprises 99% or more of a compound of Formula (I) or a salt thereof and about 1% or less of the compound of Formula (IV) or a salt thereof.

In some embodiments, the composition comprises less than about 0.5% of the compound of Formula (5). In some embodiments, the composition comprises less than about 0.4% of the compound of Formula (5). In some embodiments, the composition comprises less than about 0.3% of the compound of Formula (5). In some embodiments, the composition comprises less than about 0.2% of the compound of Formula (5). In some embodiments, the composition comprises less than about 0.1% of the compound of Formula (5). In some embodiments, the composition comprises less than about 0.05% of the compound of Formula (5). In some embodiments, the composition comprises less than about 0.01% of the compound of Formula (5).

In another aspect, disclosed herein is a composition comprising a compound of Formula (I) or a salt thereof,

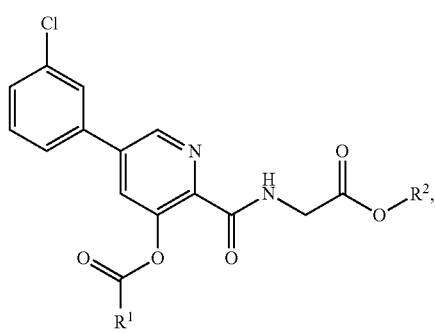

(I)

wherein $R^1$ is $C_{1-4}$ alkyl, $CH_2Cl$, phenyl, or benzyl, in which each of phenyl and benzyl may be independently substituted with one, two or three substituents selected from methyl, methoxy, nitro and halogen; $R^2$ is $C_{1-4}$ alkyl; and comprising less than about 0.5% of the compound of Formula (5):

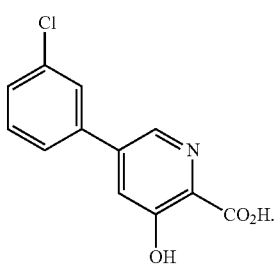

In some embodiments, the composition comprises less than about 0.4% of the compound of Formula (5). In some embodiments, the composition comprises less than about 0.3% of the compound of Formula (5). In some embodiments, the composition comprises less than about 0.2% of the compound of Formula (5). In some embodiments, the composition comprises less than about 0.1% of the compound of Formula (5). In some embodiments, the composition comprises less than 0.05% of the compound of Formula (5). In some embodiments, the composition comprises less than about 0.01% of the compound of Formula (5).

Throughout the claims and specification, unless otherwise noted, a numeric percentage point (%) of a compound refers to the purity or impurity of that compound as measured by HPLC.

Methods of Preparation

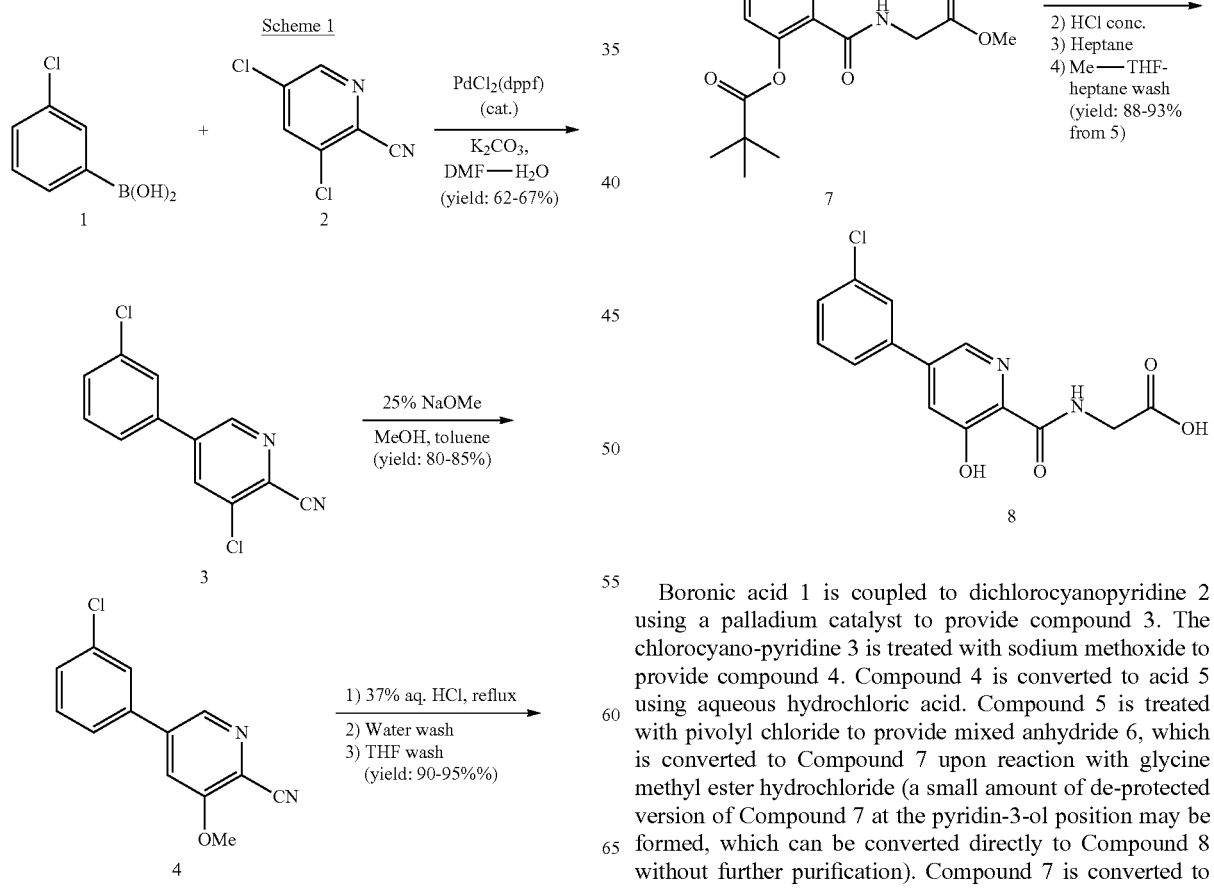

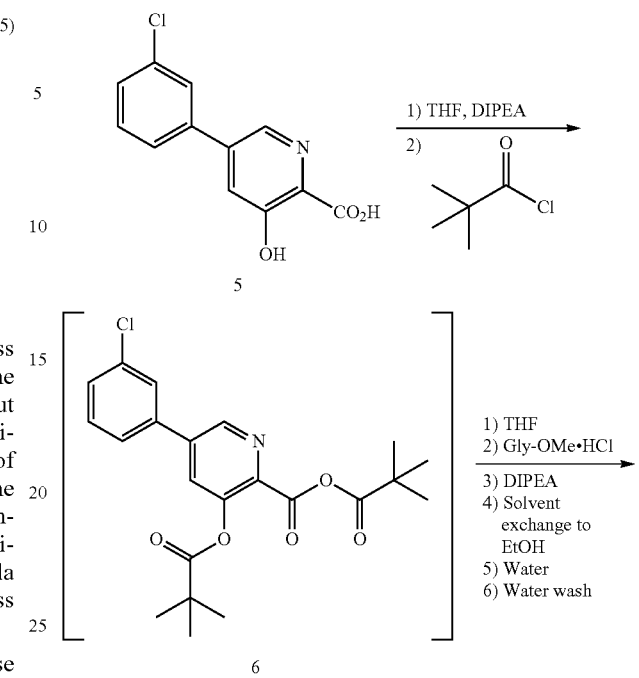

Boronic acid 1 is coupled to dichlorocyanopyridine 2 using a palladium catalyst to provide compound 3. The chlorocyano-pyridine 3 is treated with sodium methoxide to provide compound 4. Compound 4 is converted to acid 5 using aqueous hydrochloric acid. Compound 5 is treated with pivolyl chloride to provide mixed anhydride 6, which is converted to Compound 7 upon reaction with glycine methyl ester hydrochloride (a small amount of de-protected version of Compound 7 at the pyridin-3-ol position may be formed, which can be converted directly to Compound 8 without further purification). Compound 7 is converted to compound 8 using potassium hydroxide.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed with invention as defined in the claims which follow. The invention disclosed herein is further illustrated by the following examples which in no way should be construed as being limiting.

Example 1: Preparation of 5-(3-chlorophenyl)-3-chloro-2-cyanopyridine (Compound 3)

A 20 L reactor equipped with a mechanical stirrer, dip tube, thermometer and nitrogen inlet was charged with (3-chlorophenyl)boronic acid (550 g, 3.52 mol), 3,5-dichloro-2-cyanopyridine (639 g, 3.69 mol), $K_2CO_3$ (5.5 g, 40 mmol), [1,1'-bis(diphenyphosphino)ferrocene]dichloro-palladium(II) [$PdCl_2$(dppf)] (11.5 g, 140 mmol), and dimethylformamide (3894 g, 4.125 L). The reaction solution was agitated and purged with nitrogen through the dip-tube for 30 minutes. Degassed water (413 g) was then charged to the reaction mixture while maintaining a temperature of less than 50° C. 25 hours. The reaction was determined to be complete due to the disappearance of 3,5-dichloro-2-cyanopyridine as measured by TLC analysis using ethyl acetate/methanol (4:1) as the mobile phase and UV 435 nm to visualize the reaction components. The reaction solution was then cooled to 5° C. and charged with heptane (940 g, 1.375 L) and agitated for 30 minutes. Water (5.5 L) was charged and the mixture was further agitated for 1 hour as the temperature was allowed to rise to 15° C. The solid product was isolated by filtration and washed with water (5.5 L) followed by heptane (18881 g, 2750 ML). The resulting cake was air dried under vacuum for 18 hours and then triturated with a mixture of 2-propanol (6908 g, 8800 mL and heptane (1 g, 2200 mL at 50° C. for 4 hours, cooled to ambient temperature and then agitated at ambient temperature for 1 hour. The product was then isolated by filtration and washed with cold 2-propanol (3450 g, 4395 mL) followed by heptane (3010 g, 4400 mL). The resulting solid was dried under high vacuum at 40° C. for 64 hours to afford 565.9 g (65% yield) of the desired product as a beige solid. Purity by HPLC was 98.3%. $^1$H NMR (DMSO-$d_6$) δ 9.12 (d, 1H), 8.70 (d, 1H), 8.03 (t, 1H) 7.88 (m, 1H), and 7.58 (m, 2H).

Example 2: Preparation of 5-(3-chlorophenyl)-3-methoxy-2-cyanopyridine (Compound 4)

A 20 L reactor equipped with a mechanical stirred, condenser, thermometer and nitrogen inlet was charged with 5-(3-chlorophenyl)-3-chloro-2-cyanopyridine, 1, (558 g, 2.24 mol) and methanol as needed, followed by sodium methoxide (25% solution in methanol, 726.0 g, 3.36 mol). With agitation, the reaction solution was heated to reflux for 24 hours, resulting in a beige-colored suspension. The reaction was determined to be complete due to the disappearance of 5-(3-chlorophenyl)-3-chloro-2-cyanopyridine as measured by TLC analysis using hexane/ethyl acetate (6:3) as the mobile phase and UV 435 nm to visualize the reaction components. The reaction mixture was cooled to 5° C. and then charged with water (5580 mL). The resulting slurry was agitated for 3 hours at 5° C. The solid product was isolated by filtration and washed with water (5580 mL) until the filtrate had a pH of 7. The filter cake was air dried under vacuum for 16 hours. The filter cake was then charged back to the reactor and triturated in MeOH (2210 g, 2794 mL) for 1 hour at ambient temperature. The solid was collected by filtration and washed with MeOH (882 g, 1116 mL, 5° C.) followed by heptane (205 mL, 300 mL), and dried under high vacuum at 45° C. for 72 hours to afford 448 g (82% yield) of the desired product as an off-white solid. Purity by HPLC was 97.9%. $^1$H NMR (DMSO-$d_6$) δ 8.68 (d, 1H), 8.05 (d, 1H), 8.01 (s, 1H) 7.86 (m, 1H), 7.59 (s, 1H), 7.57 (s, 1H) and 4.09 (s, 3H).

Example 3: Preparation of 5-(3-chlorophenyl)-3-hydroxypyridine-2-carboxylic acid (Compound 5)

A 20 L reactor equipped with a mechanical stirrer, condenser, thermometer, nitrogen inlet and 25% aqueous NaOH trap was charged 5-(3-chlorophenyl)-3-methoxy-2-cyanopyridine, 2, (440.6 g, 1.8 mol) and 37% aqueous solution of HCl (5302 g). While being agitated, the reaction solution was heated to 102° C. for 24 hours. Additional 37% aqueous HCl (2653 g) was added followed by agitation for 18 hours at 104° C. The reaction contents was then cooled to 5° C., charged with water (4410 g) and then agitated at 0° C. for 16 hours. The resulting precipitated product was isolated by filtration and washed with water until the filtrate had a pH of 6 (about 8,000 L of water). The filter cake was pulled dry under reduced pressure for 2 hours. The cake was then transferred back into the reactor and triturated in THF (1958 g, 2201 mL) at ambient temperature for 2 hours. The solid product was then isolated by filtration and washed with THF (778 g, 875 mL) and dried under reduced pressure at 5° C. for 48 hours to afford 385 g (89% yield) of the desired product as an off-white solid. HPLC purity was 96.2%. $^1$H NMR (DMSO-$d_6$) δ 8.52 (d, 1H), 7.99 (d, 1H), 7.95 (s, 1H) 7.81 (t, 1H), 7.57 (s, 1H), and 7.55 (s, 1H).

Example 4a: Preparation of 5-(3-chlorophenyl)-2-(N-glycine methylester carboxylic amide)-3-(2,2-dimethyl-1-oxopropoxy) pyridine (Compound 7)

3-Hydroxy 5-(3-chlorophenyl)-2-carboxy-pyridine (1.00 wt) and tetrahydrofuran (4.48 wt/wt) was charged to a reactor, followed by N,N-diisopropyethylamine (1.21 wt/wt). Pivaloyl chloride (1.05 wt/wt) was added at about 0° C. and the mixture was agitated until the reaction was deemed to be completed. Tetrahydrofuran (2.59 wt/wt) and glycine methyl ester hydrochloride (0.64 wt/wt) were added at about 0° C. and N,N-diisopropyethylamine (0.78 wt/wt) was added at about 0° C. The mixture was agitated at about 0° C. and at ambient temperature until the reaction was deemed completed. The reaction solvent tetrahydrofuran was exchanged for ethanol at elevated temperature under vacuum. Water (8.00 wt/wt) was added at about 40° C. The resulting suspension was agitated at ambient temperature, filtered and washed with ethanol and water. Isolated Compound 7 contained about 0.5% of Compound 5, which was difficult to remove.

Example 4b: Preparation of 5-(3-chlorophenyl)-2-(N-glycine Methylester Carboxylic amide)-3-(2,2-dimethyl-1-oxopropoxy) pyridine (Compound 7)

3-Hydroxy 5-(3-chlorophenyl)-2-carboxy-pyridine (1.00 wt) and tetrahydrofuran (4.48 wt/wt) was charged to a reactor, followed by N,N-diisopropyethylamine (1.21 wt/wt). Pivaloyl chloride (1.05 wt/wt) was added at about 0° C. and the mixture was agitated until the reaction was deemed to be completed. Tetrahydrofuran (2.59 wt/wt) and glycine methyl ester hydrochloride (0.64 wt/wt) were added at about 0° C. and N,N-diisopropyethylamine (0.78 wt/wt) was added at about 0° C. The mixture was agitated at about 0° C. and at ambient temperature until the reaction was deemed completed. The reaction solvent tetrahydrofuran was exchanged for ethanol at elevated temperature under vacuum. Water (8.00 wt/wt) was added at about 40° C., followed by an additional amount of N,N-diisopropyethylamine (0.077 wt/wt). The suspension was agitated at ambient temperature, filtered and washed with ethanol and water. Isolated Compound 7 contained no detectable amount of Compound 5 or lower than 0.05% of Compound 5 by HPLC. Compound 7 was used for the subsequent step without further purification. $^1$H NMR (300 MHz, DMSO-$d_6$) δ 9.064 (t, j=6.1 Hz, 1H), 8.947 (d, j=2.0 Hz, 1H), 8.161 (d, j=2.0 Hz, 1H), 7.999 (m, 1H), 7.870 (m, 1H), 7.568 (m, 2H), 4.024 (d, j=6.1 Hz, 2H), 3.656 (s, 3H), 1.332 (s, 9H). The molecular weight of Compound 7 is 404.11, which was confirmed by its mass spectrum showing a main peak with a mass of 405.1, which is the [M+1] ion of the molecule.

Example 5: Preparation of 5-(3-chlorophenyl)-2-(N-glycine Carboxylic Amide)-3-hydroxypyridine (Compound 8)

5-(3-chlorophenyl)-2-(N-glycine methylester carboxylic amide)-3-(2,2-dimethyl-1-oxopropoxy) pyridine, 2-methyl-tetrahydrofuran (6.92 wt/wt) and water (3.24 wt/wt) were charged into a reactor. A potassium hydroxide solution of approximately 45% (1.50 wt/wt) was added and the mixture agitated at ambient temperature until the reaction was deemed completed. Water ((3.73 wt/wt) was charged and the mixture was acidified with concentrated aqueous HCl (about 1.3 wt/wt) at ambient temperature. The lower aqueous phase was discharged, and water was added to the organic extract at about 45° C. The lower aqueous phase was discharged and the organic phase was polish filtered. 2-Methyl-tetrahydrofuran (8.30 wt/wt) was charged and the mixture concentrated at about 45° C. under vacuum to about 5 volumes. n-Heptane (0.99 wt/wt) was and 5-(3-chlorophenyl)-2-(N-glycine carboxylic amide)-3-hydroxypyridine seeds (0.005 wt/wt) were added at about 45° C. n-Heptane (5.62 wt/wt) was charged in about 2 h and the suspension was agitated for about 1 h at about 45° C. The suspension was concentrated to about 6.5 volumes at elevated temperature under vacuum, followed by agitation at about 75° C. The suspension was cooled to ambient temperature, agitated and filtered. The wet cake was washed with n-heptane (3.31 wt/wt) and dried at about 50° C. und vacuum to yield white to beige crystals in about 90% yield and a purity of about 100% by HPLC from the charged amount of 3-hydroxy 5-(3-chlorophenyl)-2-carboxy-pyridine (Compound 5). $^1$H NMR (DMSO-$d_6$) δ 12.84 (s, 1H), 12.39 (s, 1H), 9.39 (t, 1H), 8.56 (d, 1H), 7.94 (s, 1H), 7.81 (m, 2H), 7.55 (q, 2H), and 4.02 (d, 2H).

While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A process for preparing a compound of Formula (8)

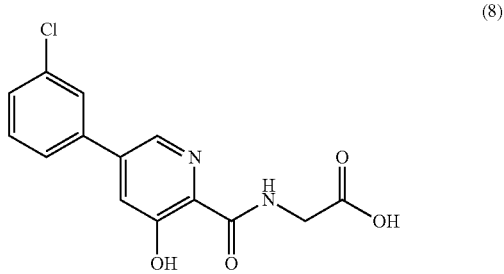 [SMILES: O=C(O)CNC(=O)c1ncc(-c2cccc(Cl)c2)cc1O]

(8)

or a salt thereof, comprising:
contacting a compound of Formula (I) or a salt thereof,

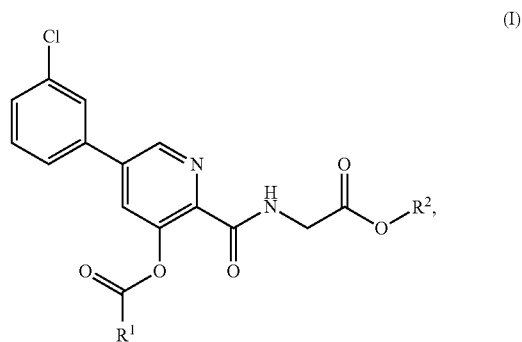

(I)

wherein:
R$^1$ is C$_{1-4}$ alkyl, CH$_2$Cl, phenyl, or benzyl, in which each of phenyl and benzyl may be independently substituted with one, two or three substituents selected from methyl, methoxy, nitro and halogen; and
R$^2$ is C$_{1-4}$ alkyl,
with a hydrolyzing agent,
wherein the compound of Formula (I) or a salt thereof is prepared by a process comprising:
a) contacting a compound of Formula (5) or a salt thereof,

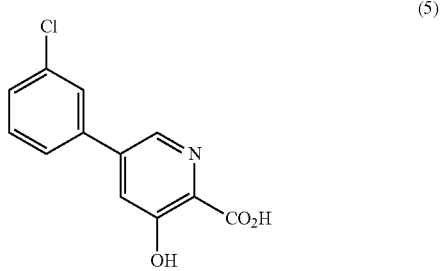 [SMILES: O=C(O)c1ncc(-c2cccc(Cl)c2)cc1O]

(5)

with a compound of Formula (II) or a salt thereof in the presence of a base,

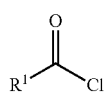
(II)

wherein R¹ is C₁₋₄ alkyl, CH₂Cl, phenyl, or benzyl, in which each of phenyl and benzyl may be independently substituted with one, two or three substituents selected from methyl, methoxy, nitro and halogen; and b) contacting a product formed in step a) with a compound of Formula (III) or a salt thereof in the presence of a base,

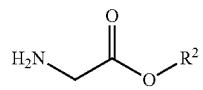
(III)

wherein R² is C₁₋₄ alkyl; and c) washing the compound of Formula (I) from step b) with a solvent comprising water and a base, to provide the compound of Formula (I) or a salt thereof,

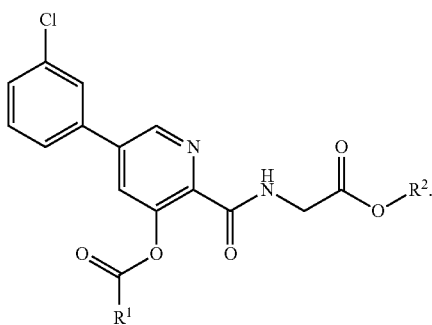
(I)

2. The process of claim 1, wherein R¹ is t-butyl and/or R² is methyl.

3. The process of claim 1, wherein the hydrolyzing agent comprises an acid or a base.

4. The process of claim 3, wherein the base is an alkali metal hydroxide, alkali metal carbonate, Polymer-SK, or tetrabutylammonium fluoride (TBAF).

5. The process of claim 3, wherein the base
is an alkali metal hydroxide selected from lithium hydroxide (LiOH), sodium hydroxide (NaOH), potassium hydroxide (KOH), cesium hydroxide (CsOH), and any combination thereof; or
is an alkali metal carbonate selected from lithium carbonate (Li₂CO₃), sodium carbonate (Na₂CO₃), potassium carbonate (K₂CO₃), cesium carbonate (Cs₂CO₃), and any combination thereof.

6. The process of claim 5, wherein the alkali metal hydroxide is potassium hydroxide (KOH).

7. The process of claim 1, which occurs in presence of a solvent comprising N,N-dimethylformide (DMF), t-butanol, dimethoxyethane (DME), acetonitrile, dichloromethane (DCM), tetrahydrofuran (THF), 2-methyltetrahydrofuran (ME-THF), isopropyl alcohol, methanol, ethanol, or any combination thereof.

8. The process of claim 7, wherein the solvent comprises 2-methyltetrahydrofuran (ME-THF).

9. The process of claim 1, wherein the purity of the compound of Formula (8) is at least 99%.

10. The process of claim 1, wherein the compound of Formula (I) comprises less than about 0.5% of the compound of Formula (5).

11. The process of claim 1, wherein each said base is independently an organic base.

12. The process of claim 11, wherein each organic base is independently triethylamine (TEA), triisopropylamine, diisopropylamine (DIPEA), pyridine, 2,6-Di-tert-butylpyridine, 1,8-Diazabicycloundec-7-ene (DBU), 1,5-Diazabicyclo(4.3.0)non-5-ene (DBN), or any combination thereof.

13. The process of claim 11, wherein each organic base is independently diisopropylamine (DIPEA).

14. The process of claim 1, which occurs in the presence of a solvent comprising ethanol, N,N-dimethylformide (DMF), diethylformamide (DEF), dimethylacetamide (DMA), diethylacetamide (DEA), dimethyl sulfoxide (DMSO), dioxane, dimethoxyethane (DME), acetonitrile, dichloromethane (DCM), tetrahydrofuran (THF), 2-methyltetrahydrofuran (ME-THF), or any combination thereof.

15. The process of claim 14, wherein the solvent is tetrahydrofuran (THF).

16. The process of claim 1, wherein R¹ is t-butyl and R² is methyl.

17. The process of claim 1, wherein R¹ is C₁₋₄ alkyl.

\* \* \* \* \*